US010328163B2

(12) United States Patent
Wester et al.

(10) Patent No.: US 10,328,163 B2
(45) Date of Patent: Jun. 25, 2019

(54) COMPOUNDS BINDING TO NEUROPATHOLOGICAL AGGREGATES

(71) Applicant: Technische Universität München, Munich (DE)

(72) Inventors: Hans-Jürgen Wester, Ilmmünster (DE); Behrooz H. Yousefi, Haar (DE)

(73) Assignee: Technische Universität München, Munich (DE)

( * ) Notice: Subject to any disclaimer, the term of this patent is extended or adjusted under 35 U.S.C. 154(b) by 0 days.

(21) Appl. No.: 15/323,552

(22) PCT Filed: Jul. 3, 2015

(86) PCT No.: PCT/EP2015/065241
§ 371 (c)(1),
(2) Date: Jan. 3, 2017

(87) PCT Pub. No.: WO2016/001422
PCT Pub. Date: Jan. 7, 2016

(65) Prior Publication Data
US 2017/0157274 A1     Jun. 8, 2017

(30) Foreign Application Priority Data
Jul. 4, 2014   (EP) .................................. 14175825

(51) Int. Cl.
A61K 51/04     (2006.01)
G01N 33/60     (2006.01)
G01N 33/68     (2006.01)

(52) U.S. Cl.
CPC ......... *A61K 51/0453* (2013.01); *G01N 33/60* (2013.01); *G01N 33/6896* (2013.01); *G01N 2333/47* (2013.01); *G01N 2333/4709* (2013.01); *G01N 2800/7047* (2013.01)

(58) Field of Classification Search
CPC ...... A61K 51/00; C07D 417/04; G01N 33/60; G01N 2333/47
See application file for complete search history.

(56) References Cited

FOREIGN PATENT DOCUMENTS

WO    WO 2010/100297    9/2010

OTHER PUBLICATIONS

Aasif Helal et al. Dual-signaling fluorescent chemosensor based on bisthiazole derivatives, Tetrahedron Letters, 51, 3531-3535. (Year: 2010).*
Agdeppa et al., "Binding characteristics of radiofluorinated 6-dialkylamino-2-naphthylethylidene derivatives as positron emission tomography imaging probes for beta-amyloid plaques in Alzheimer's disease," *J. Neurosci.*, 21:RC189, 2001.
Asuni et al., "Immunotherapy targeting pathological tau conformers in a tangle mouse model reduces brain pathology with associated functional improvements," *J. Neurosci.*, 27:9115-9129, 2007.
Bagchi et al., "Binding of the radioligand SIL23 to alpha-synuclein fibrils in Parkinson disease brain tissue establishes feasibility and screening approaches for developing a Parkinson disease imaging agent," *PloS One*, 8:e55031, 2013.
Baksalerska-Pazera et al., [Structure and role of the tau protein]. *Postepy Biochemii* 48:287-295, 2002. (English summary appended).
Barghorn et al., "Tau paired helical filaments from Alzheimer's disease brain and assembled in vitro are based on beta-structure in the core domain," *Biochemistry*, 43:1694-1703, 2004.
Berriman et al., "Tau filaments from human brain and from in vitro assembly of recombinant protein show cross-beta structure," *Proc. Acad. Sci. U.S.A.*, 100:9034-9038, 2003.
Bierer et al., Neocortical neurofibrillary tangles correlate with dementia severity in Alzheimer's disease. *Arch. Neurol.*, 52:81-88, 1995.
Bierer et al., "Neurofibrillary tangles, Alzheimer's disease and Lewy bodies," *Lancet*, 335:163, 1990.
Chang et al., "Modulation and detection of tau aggregation with small-molecule ligands," *Curr. Alzheimer Res.*, 6:409-414, 2009.
Chien et al., "Early Clinical PET Imaging Results with the Novel PHF-Tau Radioligand [F-18]-T807," *J. Alzheimers Dis.*, 34:457-468, 2013.
Couchie et al., "Primary structure of high molecular weight tau present in the peripheral nervous system," *Proc. Acad. Sci. U.S.A.*, 89:4378-4381, 1992.
Diaz-Ruiz et al., "Role of Hypertension in Aggravating Abeta Neuropathology of AD Type and Tau-Mediated Motor Impairment," *Cardiovasc. Psychiatry Neurol.*, 2009:107286, 2009.
Dickson et al., "Required techniques and useful molecular markers in the neuropathologic diagnosis of neurodegenerative diseases," *Acta Neuropathol.*, 109:14-24, 2005.
Drzezga, "Basic pathologies of neurodegenerative dementias and their relevance for state-of-the-art molecular imaging studies," *Eur. J. Nucl. Med. Mol. Imaging*, 35 Suppl 1:S4-11, 2008.
Fowler et al., "Aggregating knowledge about prions and amyloid," *Cell*, 137:20-22, 2009.
Fowler et al., "Functional amyloid—from bacteria to humans," *Trends Biochem. Sci.* 32:217-224, 2007.
Fowler et al., "Functional amyloidogenesis and cytotoxicity—insights into biology and pathology," *PLoS Biol.*, 10:e1001459, 2012.
Friedhoff et al., "Structure of tau protein and assembly into paired helical filaments," *Biochim. Biophys. Acta*, 1502:122-132, 2000.

(Continued)

*Primary Examiner* — Michael G. Hartley
*Assistant Examiner* — Jagadishwar R Samala
(74) *Attorney, Agent, or Firm* — Parker Highlander PLLC

(57) ABSTRACT

The present invention provides compounds binding to neuropathological aggregates of peptides or proteins, including aggregates such as neurofibrillary tangles (NFTs), osynuclein aggregates and other amyloid aggregates. The compounds of the present invention are useful for the detection and/or diagnosis of disorders associated with such neuropathological aggregates. In further aspects, the invention provides diagnostic compositions comprising these compounds, and methods for the preparation of radiolabeled compound from non-radiolabeled precursors.

19 Claims, 4 Drawing Sheets

(56) References Cited

OTHER PUBLICATIONS

Goedert et al., "100 years of Lewy pathology," *Nat. Rev. Neurol.*, 9:13-24, 2013.
Goedert, "Alpha-synuclein and neurodegenerative diseases," *Nat. Rev. Neurosci.*, 2:492-501, 2001.
Gotz et al., "Animal models of Alzheimer's disease and frontotemporal dementia," *Nat. Rev. Neurosci.*, 9:532-544, 2008.
Gotz et al., "Tau-targeted treatment strategies in Alzheimer's disease," *Br. J. Pharmacol.*, 165:1246-1259, 2012.
Ikonomovic et al., "X-34 labeling of abnormal protein aggregates during the progression of Alzheimer's disease," *Methods Enzymol.*, 412:123-144, 2006.
Inouye et al., "Structure of core domain of fibril-forming PHF/Tau fragments," *Biophys. J.*, 90:1774-1789, 2006.
Iqbal et al., "Mechanisms of tau-induced neurodegeneration," *Acta Neuropathol.*, 118:53-69, 2009.
Ittner et al., "Brief update on different roles of tau in neurodegeneration," *IUBMB Life* 63:495-502, 2011.
Kosik et al., "Along the way to a neurofibrillary tangle: a look at the structure of tau," *Ann. Med.*, 21:109-112, 1989.
Kotzbauer et al., "Lewy body pathology in Alzheimer's disease," *J. Mol. Neurosci.*, 17:225-232, 2001.
Landau et al., "Amyloid-beta imaging with Pittsburgh compound B and florbetapir: comparing radiotracers and quantification methods," *J. Nucl. Med.*, 54:70-77, 2013.
Li et al., "Structure, stability, and aggregation of paired helical filaments from tau protein and FTDP-17 mutants probed by tryptophan scanning mutagenesis," *J. Biol. Chem.*, 277:41390-41400, 2002.
Lockhart et al., "PIB is a non-specific imaging marker of amyloid-beta (Abeta) peptide-related cerebral amyloidosis," *Brain*, 130:2607-2615, 2007.
Love et al., "Neuropathological investigation of dementia: a guide for neurologists," *J. Neurol. Neurosurg. Psychiatr.*, 76 Suppl 5:v8-14, 2005.
Manook et al., "Small-animal PET imaging of amyloid-beta plaques with [11C]PiB and its multi-modal validation APP/PS1 mouse model of Alzheimer's disease," *PloS One*, 7:e31310, 2012.
Mudher et al., "Alzheimer's disease—do tauists and baptists finally shake hands?" *Trends Neurosci.*, 25:22-26, 2002.
Mukrasch et al., "Sites of tau important for aggregation populate {beta}-structure and bind to microtubules and polyanions," *J. Biol. Chem.*, 280:24978-24986, 2005.
Ojida et al., "Fluorescent BODIPY-based Zn(II) complex as a molecular probe for selective detection of neurofibrillary tangles in the brains of Alzheimer's disease patients," *J. Am. Chem. Soc.*, 131:6543-6548, 2009.
Okamura et al., "A novel imaging probe for in vivo detection of neuritic and diffuse amyloid plaques in the brain," *J. Mol. Neurosci.*, 24:247-255, 2004.
Okamura et al., "Quinoline and benzimidazole derivatives: candidate probes for in vivo imaging of tau pathology in Alzheimer's disease," *J. Neurosci.*, 25:10857-10862, 2005.
Ossenkoppele et al., "Longitudinal imaging of Alzheimer pathology using [11C]PIB, [18F]FDDNP and [18F]FDG PET," *Eur. J. Nucl. Med. Mol. Imaging*, 39:990-1000, 2012.
Petrou et al., "Abeta-amyloid deposition in patients with Parkinson disease at risk for development of dementia," *Neurology*, 79:1161-1167, 2012.
Rambaran et al., "Amyloid fibrils: abnormal protein assembly," *Prion*, 2:112-117, 2008.
Schweers et al., "Structural studies of tau protein and Alzheimer paired helical filaments show no evidence for beta-structure," *J. Biol. Chem.*, 269:24290-24297, 1994.
Serpell et al., "Fiber diffraction of synthetic alpha-synuclein filaments shows amyloid-like cross-beta conformation," *Proc. Nat. Acad. Sci., U.S.A.*, 97:4897-4902, 2000.
Sevcik et al., "X-ray structure of the PHF core C-terminus: insight into the folding of the intrinsically disordered protein tau in Alzheimer's disease," *FEBS Lett.*, 581:5872-5878, 2007.
Shoghi-Jadid et al., "Localization of neurofibrillary tangles and beta-amyloid plaques in the brains of living patients with Alzheimer disease," *Am. J. Geriatr. Psychiatry*, 10:24-35, 2002.
Small et al., "In vivo brain imaging of tangle burden in humans," *J. Mol. Neurosci.*, 19:323-327, 2002.
Song et al. "IMPY, a potential beta-amyloid imaging probe for detection of prion deposits in scrapie-infected mice," *Nucl. Med. Biol.*, 35:197-201, 2008.
Spillantini et al., "Microtubule-associated protein tau, heparan sulphate and alpha-synuclein in several neurodegenerative diseases with dementia," *Acta Neuropathol.*, 97:585-594, 1999.
Styren et al., "X-34, a fluorescent derivative of Congo red: a novel histochemical stain for Alzheimer's disease pathology," *J. Histochem. Cytochem.*, 48:1223-1232, 2000.
Suemoto et al., "In vivo labeling of amyloid with BF-108," *Neurosci. Res.*, 48:65-74, 2004.
Tolboom et al., "Detection of Alzheimer pathology in vivo using both 11C-PIB and 18F-FDDNP PET," *J. Nucl. Med.*, 50:191-197, 2009.
Tolboom et al., "Differential association of [11C]PIB and [18F]FDDNP binding with cognitive impairment," *Neurology*, 73:2079-2085, 2009.
Willuweit et al., "Early-onset and robust amyloid pathology in a new homozygous mouse model of Alzheimer's disease," *PloS One*, 4:e7931, 2009.
Ye et al., "In vitro high affinity alpha-synuclein binding sites for the amyloid imaging agent PIB are not matched by binding to Lewy bodies in postmortem human brain," *J. Neurochem.*, 105:1428-1437, 2008.
Yousefi et al., "Synthesis and evaluation of 11C-labeled imidazo[2,1-b]benzothiazoles(IBTs) as PET tracers for imaging beta-amyloid plaques in Alzheimer's disease," *J. Med. Chem.*, 54:949-956, 2011.
Yu et al., "Synthesis and in vitro evaluation of alpha-synuclein ligands," *Bioorg. Med. Chem.*, 20:4625-4634, 2012.
Davison et al., "Fluorinated F508-CFTR correctors and potentiators for PET imaging," *Bioorg. Med. Chem. Lett.*, 22(4):1602-1605, 2011.
Findlater et al., "Synthesis and Stucture of Boron-Bisthiazole Complexes," *Eur. J. Inorg. Chem.*, 2010(34):5379-5382, 2010.
Helal et al., "Dual-signaling fluorescent chemosensor based on bisthiazole derivatives," *Tetrahedron Lett.*, 51(27):3531-3535, 2010.
International Preliminary Report on Patentability issued in corresponding PCT Application No. PCT/EP2015/065241, dated Jan. 19, 2017.
International Search Report and Written Opinion issued in corresponding PCT Application No. PCT/EP2015/065241, dated Oct. 20, 2015.

\* cited by examiner

COMPOUNDS BINDING TO NEUROPATHOLOGICAL AGGREGATES

This application is a national phase application under 35 U.S.C. § 371 of International Application No. PCT/EP2015/065241, filed Jul. 3, 2015, which claims benefit of European Application No. 14175825.0, filed Jul. 4, 2014, the entire contents of each of which are hereby incorporated by reference.

The present invention relates to compounds suitable for diagnostic uses due to binding to neuropathological aggregates of peptides or proteins, including aggregates such as neurofibrillary tangles (NFTs), α-synuclein aggregates and other amyloid aggregates. More specifically, the compounds of the present invention are useful for the imaging, detection and/or diagnosis of disorders associated with such neuropathological aggregates. In further aspects, the invention provides diagnostic compositions comprising these compounds, and methods for the preparation of radiolabeled compound from non-radiolabeled precursors.

Neurodegenerative disorders (ND) are among the most common and disabling of diseases. It entails a progressive cognitive decline and places a huge burden on families as well as on social and medical services. Its prevalence rises with aging, and the number of patients with dementia is increasing steeply. Alzheimer's disease (AD) as the most common form of dementia, Parkinson's disease (PD), frontotemporal dementias (FTDP), Creutzfeldt-Jakob disease (CJD), Huntington's disease (HD) and Lewy body disease (DLB) are all believed to be caused by, or can be detected by measuring, abnormal aggregates of peptides or proteins that develop inside nerve cells and extracellularly.

So far, accurate diagnosis and neuropathological characterization of most of these diseases that cause dementia depends on post-mortem pathological examination (FIG. 1). However, modern molecular imaging procedures allow the contribution of molecular pathologies e.g. to Alzheimer's disease to be assessed in vivo. Recent research results on non-invasive nuclear medicine and optical imaging methods has established the proof-of-concept for the feasibility of in vivo visualizing β-amyloid plaques (Aβ). The $^{11}$C- and $^{18}$F-labeled positron emission tomography (PET) tracers ($^{11}$C $t_{1/2}$=20.3 min and $^{18}$F $t_{1/2}$=109.7 min) are under extensive preclinical and clinical assessment for imaging of such plaques. Moreover, progress in imaging of other abnormalities (Song et al., 2008, Bagchi et al., 2013, Chien et al., 2013) by means of positron emission tomography (Landau et al., 2013) or single photon emission computed tomography (SPECT) has also been reported.

In case of β-amyloid plaques imaging, despite the existence of several tracers for Aβ with PET and SPECT, there is still a clear demand for tracers with improved pharmacokinetic and binding properties which provide a specific, high contrast signal reflecting the cerebral concentration of Aβ. In combination with selective tracers, pan compounds (also referred to as pan ligands) could provide a better understanding about the relationship between different peptidic proteinaceous abnormalities in a disease. It is also assumed a pan agent that binds to all or more than one type of these neuropathological aggregates would offer the opportunity of assessment and better understanding of the role of each type of aggregate and of their combined contribution in neuropathological disorders. The histopathological post mortem examination of brain tissue provides proof of these protein aggregations which can be regarded as pathognomonical for ND e.g. AD (Drzezga, 2008).

Furthermore, the role of tau protein aggregates, in particular neurofibrillary tangles of tau (NFTs τ) has been investigated (Mudher and Lovestone, 2002, Diaz-Ruiz et al., 2009). Tau is a microtubule-associated protein (MAP), which has been associated with the integrity of the microtubular system within the neurons. It appears to be playing a role in axonal transport. The hyperphosphorylation of this protein is probably involved in the disintegration of the microtubules and the development of neurofibrillary tangle development in AD (Iqbal et al., 2009). The tau-hypothesis has also been supported by findings that the deposition of neurofibrillary tangles shows good correlation with disease severity and neuronal loss (Bierer et al., 1990, Bierer et al., 1995). As a consequence, tau-aggregations are currently actively studied as a potential target for therapy of Alzheimer's disease (Asuni et al., 2007, Ittner et al., 2011, Gotz et al., 2012). Apart from its role in Alzheimer's disease, aggregation of the tau-protein has been associated with a number of other neurodegenerative disorders, the so-called tauopathies. Among those are: the frontotemporal lobar degenerations, progressive supranuclear palsy and corticobasal degeneration. Recently, mutations in the gene encoding the tau-protein (MAPT) have been identified in FTD with Parkinsonism linked to chromosome 17 (FTDP-17) (Gotz and Ittner, 2008), these findings strongly support the role of Tau as a factor causally involved in neurodegeneration. In summary, the tau-protein and its aggregates can be regarded a factor which may be causally involved in the generation of a number of deleterious neurodegenerative disorders. They thus represent a highly important target for diagnostic and follow up of therapeutic approaches in AD.

The structure of tau-neurofibrillary tangles at the molecular-level is still not entirely clear although many efforts have been taken during last two decades for structural elucidation and relationship towards AD and other tauopathies (Kosik et al., 1989, Couchie et al., 1992, Schweers et al., 1994, Friedhoff et al., 2000, Baksalerska-Pazera and Niewiadomska, 2002, Li et al., 2002, Barghorn et al., 2004, Mukrasch et al., 2005, Inouye et al., 2006, Sevcik et al., 2007, Inner et al., 2011). First tau imaging efforts have already been initiated towards tracers allowing in vivo detection of neurofibrillary tangles. Some of the reported compounds showed also some selectivity to neurofibrillary tangles (Chang et al., 2009, Ojida et al., 2009). Imaging of tau-neurofibrillary tangles in post-mortem human AD brain tissue has been reported using [$^{18}$F]FENE and [$^{18}$F]FDDNP (Agdeppa et al., 2001, Shoghi-Jadid et al., 2002, Small et al., 2002, Tolboom et al., 2009a, Tolboom et al., 2009b, Ossenkoppele et al., 2012), [$^{18}$F]BF-108 and, BF-170 (Okamura et al., 2004, Suemoto et al., 2004, Okamura et al., 2005), X-34 (Styren et al., 2000, Ikonomovic et al., 2006), PiB (Lockhart et al., 2007) and [$^{18}$F]-T807 (Chien et al., 2013). However, some of these compounds due to the predominant binding to β-amyloid plaques and some others due to suboptimal pharmacokinetics for in vivo imaging and quantification of neuritic lesions were not further utilized.

Moreover, most of the reported Aβ plaques imaging tracers not only bind to Aβ depositions but interact to some extent with all β-pleated sheet structure depositions (Fowler et al., 2007, Fowler and Kelly, 2009, 2012). Amyloid β-pleated sheet structures are not restricted to Aβ containing lesions, but can also be formed by a range of other proteins, including some that are also common in CNS disease, such as tau and α-synuclein, which give rise to NFTs and Lewy bodies respectively (Serpell et al., 2000, Berriman et al., 2003, Rambaran and Serpell, 2008).

A number of imaging studies are now reporting data from patient populations with diseases other than AD, including frontotemporal lobar degeneration and dementia with Lewy bodies (DLB), in which NFTs and LBs, respectively, from a significant part of the pathological load. It is therefore critical that a comprehensive binding profile is assembled for tracers using experimental conditions that are relevant to the low nanomolar tissue concentrations that are attained during imaging scans (Ye et al., 2008). A high resolution in vitro autoradiography study demonstrated that, at low nanomolar concentrations of [$^3$H]PiB that are directly relevant for in vivo imaging, the ligand labeled all types of Aβ-containing lesions (diffuse plaques, classical plaques and cerebrovascular amyloid) with high affinity (Lockhart et al., 2007). Although additional labeling of NFTs was also observed, the intensity of labeling was less than that associated with the Aβ-containing pathologies.

Lewy bodies (LB) and Lewy neurites are filamentous inclusions that form in the cytoplasm of susceptible neurons are primarily associated with Parkinson's disease (PD) and DLB (Goedert, 2001, Goedert et al., 2013). However, neuropathological studies have suggested that up to 60% of AD cases also exhibit significant LB pathology (Kotzbauer et al., 2001). Factors leading to the appearance, heterogeneous morphology and neuroanatomical location of LBs are only poorly understood. The inclusions typically consist of a central core and an outer halo, with the former containing both amorphous material and filamentous structures. α-synuclein as a component of LBs and Lewy neuritis can be visualized in tissue sections using the dyes thioflavin S and Congo Red (Dickson, 2005).

Recently phenothiazine derivatives reported with binding potency toward aggregated recombinant α-synuclein fibrils in a fluorescent thioflavin T competition assay and their best compound showed affinity of $K_i$=32.10±1.25 nM in vitro to α-synuclein fibrils (Yu et al., 2012)

In view of the above, there is a continuing interest for new tracers or imaging agents with suitable pharmacokinetics in the brain combined with high stability in vivo and high binding affinity to one or combination of peptide or protein aggregate targets, such as Aβ aggregates, NFT τ, and α-synuclein aggregates.

So far, the general approach for development of tracers or imaging agent for neuropathological deposits was focused on selectivity of tracers. Nevertheless, this approach may provide only suboptimal tracers, knowing that in most of neurodegenerative and vascular diseases, two or more of these abnormalities are coexisting (Spillantini et al., 1999, Love, 2005, Petrou et al., 2012).

The approach taken herein is based on developing compounds as pan or selective ligands with improved brain uptake profile combined with high binding affinity to one or more than one peptide or protein aggregate targets as tracers or imaging agents. For good diagnostics, it is important that the physician be provided with full information that includes information as pan, summed neuropathological image, and, for pan positive cases, selective neuropathological images at onset of clinical or preclinical stages of the disease, and any relevant history. Pan ligands can provide summed information including the uptake pattern of deposits in the brain. These compounds extend the concept of the currently used Aβ-PET agents as well as selective tracers for variants of other abnormal peptidic aggregates such as tau and α-syn in living brain and thus can provide valuable additional information and can allow for earlier detection and differentiation of neurodegenerative diseases in elderly people at risk. This information may add to the known relevant history of patient and help in diagnoses or follow up cases.

From a neurobiological perspective, imaging not only Aβ but simultaneous imaging of all abnormalities, such as tau and α-syn deposits, with so called PAN-ligands would probably result in an improved detection sensitivity for the progression of dementia.

Moreover compounds provided in the context of the invention may be selective for variants of pathological aggregates of peptides or proteins, such as Aβ, τ, α-synuclein for optimizing early detection, differentiation of different isoforms of the aggregates.

The compounds in accordance with the invention, e.g. in the form of radiolabeled compounds or fluorescent-labeled compounds are suitable for in vitro and in vivo evaluation methods, extending for example from small-animal PET studies in transgenic animal models of AD and other dementia models to the high resolution ex vivo analysis of co-localization of tracers with selective fluorescent immuno-histochemistry agents on single neuropathological peptidic aggregates. Ultimately, these may transfer into human study for disease diagnostic and medication follow-up.

It has been found in the context of the present invention that the compounds and preferred compounds described below, including pharmaceutically active salts thereof, have enhanced binding properties to neuropathological aggregates, including plaques or fibrils, of peptides or proteins. Neuropathological aggregates of particular interest, for which the compounds of the invention can act as binding partners (also referred to as ligands), are β-amyloid (Aβ) aggregates, neurofibrillary tangles of tau (NFTs τ), α-synuclein aggregates, Prion ($^{Sc}$PrP), or Huntingtin. The compounds of the invention can act as Pan-ligands, i.e. ligands binding to two or more of these neuropathological aggregates, or as selective ligands binding to a specific type aggregate.

The compounds of the invention thus allow the detection or diagnosis of such neuropathological aggregates, and consequently of ND associated with these aggregates, in particular Alzheimer's disease (AD), Parkinson's disease (PD), frontotemporal dementias (FTD), Creutzfeldt-Jakob disease (CJD), Huntington's disease (HD), Lewy body disease (DLB) and related diseases.

To that extent, the present invention provides the compounds of formula (I) below and pharmaceutically acceptable salts thereof for use in a diagnostic method practiced on the human or animal body, in particular for use in the diagnosis of the neuropathological aggregates of peptides and/or proteins as discussed above, and/or the disorders associated with these aggregates as discussed above. Moreover, the invention provides a method for the detection and/or quantification of such neuropathological aggregates in vitro in a tissue sample obtained from a human or animal body. Further aspects of the invention are directed to diagnostic compositions comprising a radiolabeled compound of formula (I) or a pharmaceutically acceptable salt thereof, which compositions may contain a pharmaceutically acceptable carrier or diluent. In another aspect, the invention provides a method for the provision of a radiolabeled compound of formula (I) or a pharmaceutically acceptable salt thereof, said method comprising the conversion of a non-radiolabeled precursor compound of formula (I) or a pharmaceutically acceptable salt thereof via reaction of the non-radiolabeled precursor compound with a reactant containing a radioisotope.

The invention concerns a compound of the following formula (I) or pharmaceutically acceptable salt thereof for use in a diagnostic method practiced on the human or animal body:

wherein:
$X^1$ and $X^4$ are independently selected from CH and N, and are preferably both N;
$X^2$ and $X^3$ are independently selected from $CH_2$, S and O, preferably selected from S and O and are further preferably both S;
$R^1$ and $R^2$ are independently selected from F, I, Br, and At, preferably from F and I, and m and n are integers independently selected from 0 and 1, and are more preferably 0;
$Ar^1$ and $Ar^2$ are independently selected from aryl and heteroaryl,
$Ar^1$ and $Ar^2$ each being optionally substituted by one or more substituents selected, independently for each occurrence, from halogen, hydroxy, nitro, cyano, alkyl, haloalkyl, alkenyl, alkynyl, amino, alkylaryl, alkylamino, alkylamine, alkoxy, aryloxy;
—O—$CH_2$—$CH_2)_o$—$R^{10}$, wherein $R^{10}$ is selected from —H, —OH, —$OSO_2$alkyl, —$OSO_2$aryl, and —F, and o is an integer from 1 to 4;
—$NR^{11}$COOalkyl, —$NR^{11}$COOarylCOalkyl, —$NR^{11}$COaryl;
—COOalkyl, —COOaryl, —COalkyl, —COaryl, aryl, cycloalkyl;
cycloalkylamino-, -cycloalkylamine, heterocycle, a fluorescent label;
and —Z—$R^{12}$ substitutions, wherein Z is selected from O, $NR^{13}$, NH and S;
and wherein $R^{11}$, $R^{12}$ and $R^{13}$ are independently selected from H, $C_nH_{2n+1}$, $C_nH_{2n}$-hal, with n being an integer of 1 to 3, —$CH_2$—CH=CH-hal, and —[$CH_2$—$CH_2$—O]$_p$—[$CH_2$—$CH_2$]$_q$-hal, wherein hal is selected from F, Cl, I, Br, and At, preferably from F, I and Br, and is more preferably F, p is an integer of 1 to 3 and q is 1 or 2;
wherein suitable pairs of substituents attached to adjacent ring members of $Ar^1$ or $Ar^2$, respectively, can be combined to form a ring fused with $Ar^1$ or $Ar^2$;
and wherein the compound of formula (I) or the pharmaceutically acceptable salt thereof may be a radiolabeled compound wherein one or more groups selected from $R^1$, $R^2$, a substituent attached to $Ar^1$ and a substituent attached to $Ar^2$ contain a radioisotope of an element which is present therein.

$R^1$ and $R^2$ are independently selected from F, I, Br, and At, preferably from F and I. The variables m and n are integers independently selected from 0 and 1, and are more preferably 0. Thus, as will be understood by the skilled person, $R^2$ is a substituent which may be present once (m=1) and replaces a hydrogen atom that would be attached to a suitable ring member in the ring containing $X^1$ and $X^2$, or which may be absent (m=0). Similarly, $R^1$ is a substituent which may be present once (n=1) and replaces a hydrogen atom that would be attached to a suitable ring member in the ring containing $X^3$ and $X^4$, or which may be absent (n=0). It will also be understood from the above formula that, if $R^2$ is present, it will not be attached to the same ring member as $Ar^1$ and that if $R^1$ is present, it will not be attached to the same ring member as $Ar^2$. Preferably, m and n are 0, i.e. $R^1$ and $R^2$ are absent.

As indicated in the formula, $Ar^1$ and $Ar^2$ are each present once in the compounds of formula (I). As will be understood by the skilled person, $Ar^1$ is a substituent which replaces a hydrogen atom that would be attached to a suitable ring member in the ring containing $X^1$ and $X^2$, and $Ar^2$ is a substituent which replaces a hydrogen atom that would be attached to a suitable ring member in the ring containing $X^3$ and $X^4$. It is preferred that $Ar^1$ is attached to the ring carbon atom adjacent to $X^1$, and that $Ar^2$ is attached to the ring carbon atom adjacent to $X^4$. $Ar^1$ and $Ar^2$ are independently selected from aryl and heteroaryl, preferably from phenyl and from a 5- or 6-membered heteroaryl.

Each of $Ar^1$ and $Ar^2$ is optionally substituted by one or more substituents as defined above. Preferred substituents for $Ar^1$ and $Ar^2$ are selected, independently for each occurrence, from halogen, hydroxy, alkyl, haloalkyl, alkenyl, alkynyl, alkylamino, alkylamine, alkoxy, —(O—$CH_2$—$CH_2)_o$—$R^{10}$ wherein $R^{10}$ is selected from —H, —OH, —$OSO_2$alkyl, —$OSO_2$aryl, and —F, and o is an integer from 1 to 4,
and —Z—$R^{12}$ substitutions where Z is selected from O, $NR^{13}$, NH and S, and wherein $R^{12}$ and $R^{13}$ are independently selected from H, $C_nH_{2n+1}$, $C_nH_{2n}$-hal, with n being an integer of 1 to 3, —$CH_2$—CH=CH-hal, and —[$CH_2$—$CH_2$—O]$_p$—[$CH_2$—$CH_2$]$_q$-hal, wherein hal is selected from F, Cl, I, Br, and At, preferably from F, I and Br, and is more preferably F, p is an integer of 1 to 3 and q is 1 or 2.

Moreover, as noted above, suitable pairs of substituents attached to adjacent ring members of $Ar^1$ or $Ar^2$, respectively, can be combined to form a ring fused with $Ar^1$ or $Ar^2$. As a preferred example of such combined substituents, a pair of adjacent substituents may form a group —O—$(CH_2)_r$—O— attached to adjacent ring members of $Ar^1$ or $Ar^2$ to form a heterocycle fused to $Ar^1$ or $Ar^2$, wherein r is 1 or 2, preferably 1.

It is preferred that each of $Ar^1$ and $Ar^2$ carries at least one of the substituents or preferred substituents defined above. As regards the number of substituents, it is preferred that each of $Ar^1$ and $Ar^2$ is substituted by a maximum of 3 of the substituents or preferred substituents defined above. It is more preferred that each of $Ar^1$ and $Ar^2$ is substituted by 1 or 2 of these substituents. As regards the position of the substituent(s) attached to $Ar^1$ and $Ar^2$, it is preferred that the ortho-positions of $Ar^1$ relative to the bond between $Ar^1$ and the ring containing $X^1$ and $X^2$ are free of a substituent, and that the ortho-positions of $Ar^2$ relative to the bond between $Ar^2$ and the ring containing $X^3$ and $X^3$ are free of a substituent.

Thus, generally preferred compounds of formula (I) or pharmaceutically acceptable salts thereof are those wherein:
$X^1$ and $X^4$ are both N;
$X^2$ and $X^3$ are independently selected from S and O;
$R^1$ and $R^2$ are independently selected from F, I, Br, and At, preferably from F and I, and m and n are integers independently selected from 0 and 1, and are more preferably 0;
$Ar^1$ and $Ar^2$ are independently selected from phenyl and 5- or 6-membered heteroaryl,
$Ar^1$ and $Ar^2$ each being optionally substituted by one or more substituents, and preferably each being substituted by one or two substituents, selected independently for each occurrence, from halogen, hydroxy, nitro, cyano, alkyl, haloalkyl, alkenyl, alkynyl, amino, alkylaryl, alkylamino, alkylamine, alkoxy, aryloxy;

—(O—CH$_2$—CH$_2$)$_o$—R$^{10}$, wherein R$^{10}$ is selected from —H, —OH, —OSO$_2$alkyl, —OSO$_2$aryl, and —F, and o is an integer from 1 to 4;
—NR$^{11}$COOalkyl, —NR$^{11}$COOarylCOalkyl, —NR$^{11}$COaryl;
—COOalkyl, —COOaryl, —COalkyl, —COaryl, aryl, cycloalkyl;
cycloalkylamino-, -cycloalkylamine, heterocycle, a fluorescent label;
and —Z—R$^{12}$ substitutions, wherein Z is selected from O, NR$^{13}$, NH and S;
and wherein R$^{11}$, R$^{12}$ and R$^{13}$ are independently selected from H, C$_n$H$_{2n+1}$, C$_n$H$_{2n}$-hal, with n being an integer of 1 to 3, —CH$_2$—CH═CH-hal, and —[CH$_2$—CH$_2$—O]$_p$—[CH$_2$—CH$_2$]$_q$-hal, wherein hal is selected from F, Cl, I, Br, and At, preferably from F, I and Br, and is more preferably F, p is an integer of 1 to 3 and q is 1 or 2;
wherein suitable pairs of substituents attached to adjacent ring members of Ar$^1$ or Ar$^2$, respectively, can be combined to form a ring fused with Ar$^1$ or Ar$^2$;
and wherein the compound of formula (I) or the pharmaceutically acceptable salt thereof may be a radiolabeled compound wherein one or more groups selected from R$^1$, R$^2$, a substituent attached to Ar$^1$ and a substituent attached to Ar$^2$ contain a radioisotope of an element which is present therein.

The compounds of formula (I) for use in the context of the present invention are more preferably compounds of the following formula (II) or pharmaceutically acceptable salts thereof:

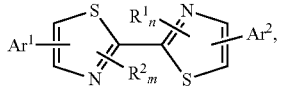

(II)

wherein Ar$^1$, Ar$^2$, R$^1$, R$^2$, m and n are defined as in formula (I), including all preferred definitions, except that where X$^1$ and X$^4$ or X$^2$ and X$^3$ are referred to in these definitions, they are replaced by the concrete ring members N or S present in the respective positions in formula (II), and wherein the compound of formula (II) or the pharmaceutically acceptable salt thereof may be a radiolabeled compound wherein one or more groups selected from R$^1$, R$^2$, a substituent attached to Ar$^1$ and a substituent attached to Ar$^2$ contain a radioisotope of an element which is present therein.

Also in the compounds of formula (II), Ar$^1$ and Ar$^2$ are each present once, and replace each a hydrogen atom in the ring to which they are attached. Ar$^1$ and Ar$^2$ are independently selected from aryl and heteroaryl, preferably from phenyl and from a 5- or 6-membered heteroaryl. It is preferred that Ar$^1$ and Ar$^2$ are attached to the ring carbon atom adjacent to N in the respective thiazole rings to which Ar$^1$ and Ar$^2$ are attached as substituents.

R$^1$ and R$^2$ are independently selected from F, I, Br, and At, preferably from F and I. The variables m and n are integers independently selected from 0 and 1, and are more preferably 0. Thus, as will be understood by the skilled person, R$^2$ is a substituent which may be present once (m=1) and replaces a hydrogen atom that would be attached to a suitable ring member in the thiazole ring, or which may be absent (m=0). Similarly, R$^1$ is a substituent which may be present once (n=1) and replaces a hydrogen atom that would be attached to a suitable ring member in the thiazole ring, or which may be absent (n=0). It will also be understood from the above formula that, if R$^2$ is present, it will not be attached to the same ring member as Ar$^1$ and that if R$^1$ is present, it will not be attached to the same ring member as Ar$^2$, Preferably, m and n are 0, i.e. R$^1$ and R$^2$ are absent.

Each of Ar$^1$ and Ar$^2$ is optionally substituted by one or more substituents as defined above for formula (I). Preferred substituents for Ar$^1$ and Ar$^2$ are selected, independently for each occurrence, from halogen, hydroxy, alkyl, haloalkyl, alkenyl, alkynyl, alkylamino, alkylamine, alkoxy,
—(O—CH$_2$—CH$_2$)$_o$—R$^{10}$ wherein R$^{10}$ is selected from —H, —OH, —OSO$_2$alkyl, —OSO$_2$aryl, and —F, and o is an integer from 1 to 4;
and —Z—R$^{12}$ substitutions where Z is selected from O, NR$^{13}$, NH and S, and wherein R$^{12}$ and R$^{13}$ are independently selected from H, C$_n$H$_{2n+1}$, C$_n$H$_{2n}$-hal, with n being an integer of 1 to 3, —CH$_2$—CH═CH-hal, and —[CH$_2$—CH$_2$—O]$_p$—[CH$_2$—CH$_2$]$_q$-hal, wherein hal is selected from F, Cl, I, Br, and At, preferably from F, I and Br, and is more preferably F, p is an integer of 1 to 3 and q is 1 or 2.

Moreover, as noted above, suitable pairs of substituents attached to adjacent ring members of Ar$^1$ or Ar$^2$, respectively, can be combined to form a ring fused with Ar$^1$ or Ar$^2$. As a preferred example of such combined substituents, a pair of adjacent substituents may form a group —O—(CH$_2$)$_r$—O— attached to adjacent ring members of Ar$^1$ or Ar$^2$ to form a heterocycle fused to Ar$^1$ or Ar$^2$, wherein r is 1 or 2, preferably 1.

It is preferred that each of Ar$^1$ and Ar$^2$ carries at least one of the substituents or preferred substituents defined above. As regards the number of substituents, it is preferred that each of Ar$^1$ and Ar$^2$ is substituted by a maximum of 3 of the substituents or preferred substituents defined above. It is more preferred that each of Ar$^1$ and Ar$^2$ is substituted by 1 or 2 of these substituents. As regards the position of the substituent(s) attached to Ar$^1$ and Ar$^2$, it is preferred that the ortho-positions of Ar$^1$ relative to the bond between Ar$^1$ and the thiazole ring of formula (II) are free of a substituent, and that the ortho-positions of Ar$^2$ relative to the bond between Ar$^2$ and the thiazole ring of formula (II) are free of a substituent.

In line with the above, generally preferred compounds of formula (II) or pharmaceutically acceptable salts thereof are those wherein:
R$^1$ and R$^2$ are independently selected from F, I, Br, and At, preferably from F and I, and m and n are integers independently selected from 0 and 1, and are more preferably 0;
Ar$^1$ and Ar$^2$ are independently selected from phenyl and 5- or 6-membered heteroaryl,
Ar$^1$ and Ar$^2$ each being optionally substituted by one or more substituents, and preferably each being substituted by one or two substituents, selected independently for each occurrence, from halogen, hydroxy, nitro, cyano, alkyl, haloalkyl, alkenyl, alkynyl, amino, alkylaryl, alkylamino, alkylamine, alkoxy, aryloxy;
—(O—CH$_2$—CH$_2$)$_o$—R$^{10}$, wherein R$^{10}$ is selected from —H, —OH, —OSO$_2$alkyl, —OSO$_2$aryl, and —F, and o is an integer from 1 to 4;
—NR$^{11}$COOalkyl, —NR$^{11}$COOarylCOalkyl, —NR$^{11}$COaryl;
—COOalkyl, —COOaryl, —COalkyl, —COaryl, aryl, cycloalkyl;
cycloalkylamino-, -cycloalkylamine, heterocycle, a fluorescent label;
and —Z—R$^{12}$ substitutions, wherein Z is selected from O, NR$^{13}$, NH and S;
and wherein R$^{11}$, R$^{12}$ and R$^{13}$ are independently selected from H, C$_n$H$_{2n+1}$, C$_n$H$_{2n}$-hal, with n being an integer of 1 to 3, —CH$_2$—CH=CH-hal, and —[CH$_2$—CH$_2$—O]$_p$—[CH$_2$—CH$_2$]$_q$-hal, wherein hal is selected from F, Cl, I, Br, and At, preferably from F, I and Br, and is more preferably F, p is an integer of 1 to 3 and q is 1 or 2;

wherein suitable pairs of substituents attached to adjacent ring members of Ar$^1$ or Ar$^2$, respectively, can be combined to form a ring fused with Ar$^1$ or Ar$^2$;

and wherein the compound of formula (II) or the pharmaceutically acceptable salt thereof may be a radiolabeled compound wherein one or more groups selected from R$^1$, R$^2$, a substituent attached to Ar$^1$ and a substituent attached to Ar$^2$ contain a radioisotope of an element which is present therein.

Still further preferred among the compounds of formula (I) are the compounds of formula (III) or pharmaceutically acceptable salts thereof:

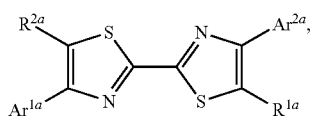

(III)

wherein
R$^{1a}$ and R$^{2a}$ are independently selected from H, F, I, Br, and At, preferably from H and F, and are more preferably H;
Ar$^{1a}$ and Ar$^{2a}$ are independently selected from aryl and heteroaryl, and are preferably aryl, and
Ar$^{1a}$ and Ar$^{2a}$ are optionally substituted by one or more substituents selected, independently for each occurrence, from halogen, hydroxy, alkyl, haloalkyl, alkenyl, alkynyl, alkylamino, alkylamine, alkoxy,
—(O—CH$_2$—CH$_2$)$_o$—R$^{10}$ wherein R$^{10}$ is selected from —H, —OH, —OSO$_2$alkyl, —OSO$_2$aryl, and —F, and o is an integer from 1 to 4;
and —Z—R$^{12}$ substitutions where Z is selected from O, NR$^{13}$, NH and S, and wherein R$^{12}$ and R$^{13}$ are independently selected from H, C$_n$H$_{2n+1}$, C$_n$H$_{2n}$-hal, with n being an integer of 1 to 3, —CH$_2$—CH=CH-hal, and —[CH$_2$—CH$_2$—O]$_p$—[CH$_2$—CH$_2$]$_q$-hal, wherein hal is selected from F, Cl, I, Br, and At, preferably from F, I and Br, and is more preferably F, p is an integer of 1 to 3 and q is 1 or 2;
wherein suitable pairs of substituents attached to adjacent ring members of Ar$^{1a}$ or Ar$^{2a}$, respectively, can be combined to form a ring fused with Ar$^{1a}$ or Ar$^{2a}$;
and wherein the compound of formula (III) or the pharmaceutically acceptable salt thereof may be a radiolabeled compound wherein one or more groups selected from R$^{1a}$, R$^{2a}$, a substituent attached to Ar$^{1a}$ and a substituent attached to Ar$^{2a}$ contain a radioisotope of an element which is present therein.

As noted above, Ar$^{1a}$ and Ar$^{2a}$ are independently selected from aryl and heteroaryl, and are preferably aryl. Preferred as aryl group is phenyl, and preferred as heteroaryl group is a 5- or 6-membered heteroaryl. It is preferred that each of Ar$^{1a}$ and Ar$^{2a}$ carries at least one of the substituents or preferred substituents defined above. As regards the number of substituents, it is preferred that each of Ar$^{1a}$ and Ar$^{2a}$ is substituted by a maximum of 3 of the substituents listed above. It is more preferred that each of Ar$^{1a}$ and Ar$^{2a}$ is substituted by 1 or 2 of these substituents. As regards the position of the substituent(s) attached to Ar$^{1a}$ and Ar$^{2a}$, it is preferred that the ortho-positions of Ar$^{1a}$ relative to the bond between Ar$^{1a}$ and the thiazole ring of formula (III) are free of a substituent, and that the ortho-positions of Ar$^{2a}$ relative to the bond between Ar$^{2a}$ and the thiazole ring of formula (III) are free of a substituent.

As noted above, suitable pairs of substituents attached to adjacent ring members of Ar$^{1a}$ or Ar$^{2a}$, respectively, can be combined to form a ring fused with Ar$^{1a}$ or Ar$^{2a}$. As a preferred example, a pair of adjacent substituents may form a group —O—(CH$_2$)$_r$—O— attached to adjacent ring members of Ar$^{1a}$ or Ar$^{2a}$ to form a heterocycle fused to Ar$^{1a}$ or Ar$^{2a}$, wherein r is 1 or 2, preferably 1.

Even further preferred are the compounds of formula (IV) or pharmaceutically acceptable salts thereof:

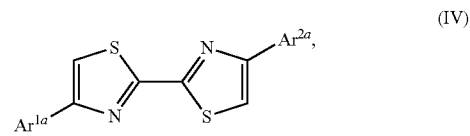

(IV)

wherein Ar$^{1a}$ and Ar$^{2a}$ are defined as for formula (III), and wherein the compound of formula (IV) or the pharmaceutically acceptable salt thereof may be a radiolabeled compound wherein one or more groups selected from a substituent attached to Ar$^{1a}$ and a substituent attached to or Ar$^{2a}$ contain a radioisotope of an element which is present therein Particularly preferred among the compounds of formula (I) are the compounds of formula (V) or pharmaceutically acceptable salts thereof:

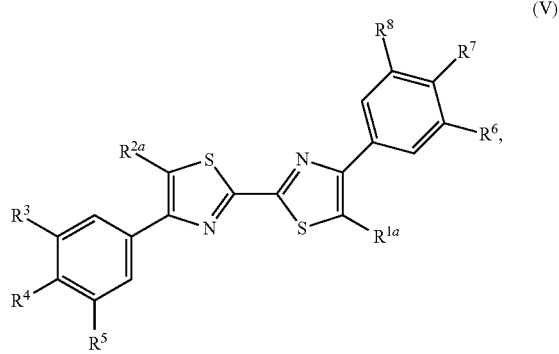

(V)

and most preferred are those of formula (VI) or pharmaceutically acceptable salts thereof:

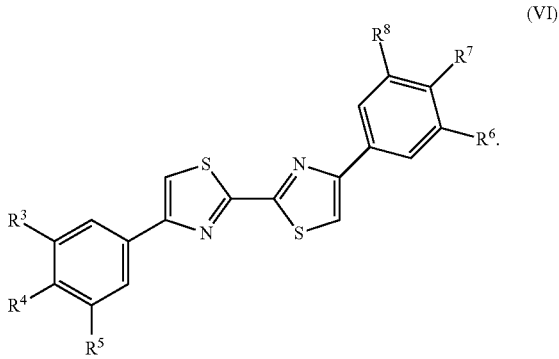

(VI)

In formula (V), R$^{1a}$ and R$^{2a}$ are independently selected from H, F, I, Br, and At, preferably from H and F, and are most preferably H.

In formulae (V) and (VI), $R^3$ to $R^8$ are independently selected from hydrogen, halogen, hydroxy, alkyl, alkoxy, —(O—CH$_2$—CH$_2$)$_o$—R$^{10}$, wherein $R^{10}$ is selected from —H, —OH, —OSO$_2$alkyl, —OSO$_2$aryl, and —F, and o is an integer from 1 to 4, and $Z^a$—$R^{12a}$ substitutions, where $Z^a$ is selected from O, NR$^{13a}$, and NH, and wherein $R^{12a}$ and $R^{13a}$ are independently selected from H, C$_n$H$_{2n+1}$, and C$_n$H$_{2n}$-hal, with n being an integer of 1 to 3, and —[CH$_2$—CH$_2$—O]$_p$—[CH$_2$—CH$_2$]$_q$-hal, wherein hal is selected from F and I and is preferably F, p is an integer of 1 to 3 and q is 1 or 2;

or pairs of adjacent substituents $R^3$ to $R^8$ may form a group —O—(CH$_2$)$_r$—O— attached to adjacent ring members of the ring to which they are attached to form a heterocycle fused to the ring to which they are attached, wherein r is 1 or 2, preferably 1.

The compounds of formulae (V) or (IV) or the pharmaceutically acceptable salt thereof may be radiolabeled compounds wherein one or more groups selected from $R^{1a}$, $R^{2a}$ (in formula (V)), $R^3$, $R^4$, $R^5$, $R^6$, $R^7$ and $R^8$ contain a radioisotope of an element which is present therein.

It is particularly preferred in formula (V) and (VI) that one or two of $R^3$ and $R^5$, and one or two of $R^6$ and $R^8$ are H, and the other groups $R^3$ to $R^8$ are independently selected from, halogen, hydroxy, alkyl, —(O—CH$_2$—CH$_2$)$_o$—R$^{10}$ wherein $R^{10}$ is selected from —H, —OH, —OSO$_2$alkyl, —OSO$_2$aryl, and —F, and o is an integer from 1 to 4, and —$Z^a$—$R^{12a}$ substitutions, where $Z^a$ is selected from O, NR$^{13a}$, and NH, and wherein $R^{12a}$ and $R^{13a}$ are independently selected from H, C$_n$H$_{2n+1}$, and C$_n$H$_{2n}$-hal with n being an integer preferably of 1 to 3, and —[CH$_2$—CH$_2$—O]$_p$—[CH$_2$—CH$_2$]$_q$-hal, wherein hal is selected from F and I and is in particular F, p is an integer of 1 to 3 and q is 1 or 2;

or pairs of adjacent substituents $R^3$ to $R^8$ may form a group —O—(CH$_2$)$_r$—O— attached to adjacent ring members of the ring to which they are attached to form a heterocycle fused to the ring to which they are attached, wherein r is 1 or 2, preferably 1;

and wherein the compounds of formulae (V) or (IV) or the pharmaceutically acceptable salt thereof may be radiolabeled compounds wherein one or more groups selected from $R^{1a}$, $R^{2a}$, (in formula (V)), $R^3$, $R^4$, $R^5$, $R^6$, $R^7$ and $R^8$ contain a radioisotope of an element which is present therein.

As used herein, "alkyl", used alone or in combination, represents a straight or branched chain saturated hydrocarbon group which does not comprise any carbon-to-carbon double bonds or carbon-to-carbon triple bonds. Generally preferred, unless indicated otherwise in a particular context, are C1-6 alkyl groups, and in particular methyl or ethyl.

The term "alkoxy", as used herein, defines a group —O-alkyl, wherein alkyl is defined as above, including preferred embodiments.

As used herein, "alkenyl" represents a straight or branched chain unsaturated hydrocarbon group comprising one or more than one (such as two or three) carbon-to-carbon double bond(s) which does not comprise any carbon-to-carbon triple bonds.

As used herein, "alkynyl" represents a straight or branched chain unsaturated hydrocarbon group comprising one or more than one (such as two or three) carbon-to-carbon triple bond(s). It will be understood that an "alkynyl" may also comprise one or more than one (such as two or three) carbon-to-carbon double bonds.

As used herein, "aryl" represents an aromatic hydrocarbon ring, preferably a 6 to 10-membered ring, including bridged ring or fused ring systems. Preferred as aryl groups are monocyclic groups with 6 ring members or fused bicyclic groups with 9 or 10 ring members. Thus, generally preferred embodiments of "aryl" are phenyl or naphthyl, and particularly preferred is phenyl.

As used herein, "heteroaryl" represents an aromatic ring, preferably a 5-14 membered ring (unless a different number of ring members is indicated in a specific context), including bridged ring or fused ring systems, comprising one or more (such as, e.g., one, two, or three) ring heteroatoms independently selected from O, S, and N. Preferred as heteroaryl groups are monocyclic groups with 5 or 6 members and fused bicyclic groups with 8 to 10 ring members. "Heteroaryl" may, for example, refer to thienyl (thiophenyl), benzo[b]thienyl, naphtho[2,3-b]thienyl, thianthrenyl, furyl (furanyl), isobenzofuranyl, chromenyl, xanthenyl, phenoxathiinyl, pyrrolyl (including, without limitation, 2H-pyrrolyl), imidazolyl, pyrazolyl, pyridyl (pyridinyl; including, without limitation, 2-pyridyl, 3-pyridyl, and 4-pyridyl), pyrazinyl, pyrimidinyl, pyridazinyl, indolizinyl, isoindolyl, indolyl (including, without limitation, 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, phenanthrolinyl (including, without limitation, [1,10]phenanthrolinyl, [1,7]phenanthrolinyl, and [4,7]phenanthrolinyl), phenazinyl, isothiazolyl, phenothiazinyl, oxazolyl, isoxazolyl, furazanyl, phenoxazinyl, pyrazolo[1,5-a]pyrimidinyl (including, without limitation, pyrazolo[1,5-a]pyrimidin-3-yl), 1,2-benzoisoxazol-3-yl, or benzimidazolyl. More preferred as heteroaryl groups are 5- or 6-membered aromatic rings, and most preferred as heteroaryl groups are 5- or 6-membered aromatic rings comprising one or two ring heteroatoms independently selected from O, S, and N.

As used herein, "cycloalkyl" represents a saturated hydrocarbon ring, preferably a 3-11 membered ring (unless a different number of ring members is indicated in a specific context), including bridged ring, spiro ring or fused ring systems. "Cycloalkyl" may, for example, refer to cyclopropyl, cyclobutyl, cyclopentyl, cyclohexyl, or cycloheptyl. Preferred as cycloalkyl groups are monocyclic groups with 5 or 6 ring members or fused bicyclic groups with 9 or 10 ring members.

As used herein, a "heterocyclic group" or "heterocycle" represents a ring containing carbon atoms and one or more (such as, e.g., one, two, or three) heteroatoms independently selected from O, S, and N as ring members, preferably a 3-14-membered ring, including bridged ring, spiro ring or fused ring systems. The rings may be saturated or unsaturated. Preferred are monocyclic groups with 5 or 6 or fused bicyclic rings with 8 to 10 ring members.

As used herein, "alkylaryl" (or "alkaryl"), refers to an alkyl group as defined above wherein a hydrogen atom is substituted by an aryl group as defined above. Preferred as the alkyl part of the alkylaryl group is a linear C1-C6 alkyl group, carrying one aryl group at the terminal facing away from the site at which the alkyl group is bound to the remaining molecule. Preferred as the aryl part of the alkylaryl group is a naphtyl or phenyl group, and particularly preferred is a phenyl group.

The term "alkylamino" as used herein refers to an amino (i.e. —NH$_2$) group, wherein one or both hydrogen atoms are substituted by an alkyl group as defined above.

The term "alkylamine" as used herein refers to an alkyl group as defined above, wherein one or more, preferably one, hydrogen atom is replaced by an amino (—NH$_2$) group.

The term "cycloalkylamino" as used herein refers to an amino (i.e. —NH$_2$) group, wherein one or both hydrogen atoms, preferably one hydrogen atom, is substituted by a cycloalkyl group as defined above.

The term "cycloalkylamine" as used herein refers to a cycloalkyl group as defined above, wherein one or more, preferably one, hydrogen atom is replaced by an amino (—NH$_2$) group.

As used herein, "halogen" or "halo", used alone or in combination, represents F, Cl, Br, I or At, preferably F, Br, I or At, more preferably F or I, and most preferably F.

As used herein, "haloalkyl" refers to an alkyl group as defined above, wherein one or more, preferably 1 to 3, hydrogen atoms are substituted by a halogen as defined above.

As used herein, the term "fluorescent label" refers to a group which can be detected in a fluorescence reading instrument, such as a fluorescence microscope or a flow cytometer. Various fluorescent dyes are known to the skilled person for this purpose, including cyanine, fluorescein, or rhodamine.

It will be understood that, in line with common practice in the art, a substituent (such as Ar$^1$, Ar$^2$, R$^1$ and R$^2$ in formula (I) or (II)) of a cyclic moiety which is indicated in a valence bond formula with a bond directed to the cyclic moiety, but not to a specific ring member of the cyclic moiety, can be attached to any member of the cyclic moiety which can carry a substituent, including e.g. the groups X$^1$ to X$^4$, where they provide a CH moiety in the cyclic structures of formula (I).

As noted above, pharmaceutically acceptable salts of the compounds of formula (I) (including the preferred formulae I) are also suitable for use in the context of the invention. It will be understood that these salts may be formed, e.g., by protonation of an atom carrying an electron lone pair which is susceptible to protonation, such as an amino group, with an inorganic or organic acid. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

The present invention provides the compounds of formula (I) for use in a diagnostic method practiced on the human or animal body. It will be understood that, unless indicated otherwise, reference to the compounds of formula (I) or the compounds of the invention herein includes the preferred embodiments thereof as defined by formulae (II) to (VI), as well as the pharmaceutically acceptable salts thereof. The diagnosis involves the detection of neuropathological aggregates of peptides or proteins, in particular β-amyloid (Aβ) aggregates, neurofibrillary tangles of tau (NFTs τ), α-synuclein aggregates, Prion ($^{Sc}$PrP), or Huntingtin. The targets of most interest for the compounds of the invention are β-amyloid (Aβ) aggregates, neurofibrillary tangles of tau (NFTs τ), or α-synuclein aggregates.

As will be understood from the above explanation, the compounds of the present invention are able to bind, upon administration to the human or animal patient, as tracers or imaging agents to such neuropathological aggregates of peptides or proteins, and can subsequently be detected in the body of the patient, e.g. via nuclear medicine imaging, fluorescence, optical or photoacoustic methods, preferably nuclear medicine.

The compounds of the invention can thus be used in particular for the diagnosis of a pathological condition associated with the formation of neuropathological aggregates of peptides or proteins, in particular Alzheimer's disease (AD) and Alzheimer's disease related dementia, Parkinson's disease (PD) and Parkinson's disease related dementia, frontotemporal dementias (FTDP), Creutzfeldt-Jakob disease (CJD) and Creutzfeldt-Jakob disease related dementia, Huntington's disease (HD) and Huntington's disease related dementia, and Lewy body disease (DLB) and Lewy body disease related dementia.

Conditions of most interest are Alzheimer's disease (AD) and Alzheimer's disease related dementia, Parkinson's disease (PD) and Parkinson's disease related dementia.

Diagnosis includes preclinical diagnosis and clinical evaluation, e.g. for tracking progression of such neuropathological aggregates, and/or the pathological conditions associated with the formation of neuropathological aggregates The compounds of the invention can thus be used for non-invasive detection and quantification of the aggregates in animals or humans affected or suspicious of being affected with the above pathological conditions, or in transgenic disease models that are characterized in the generation of such aggregates.

For an in vivo diagnosis on the body of a human or animal, the compounds of the invention can be administered e.g. intravenously as injectable solution, typically as an aqueous solution, to a human or an animal.

Moreover, the invention provides an in vitro method for the detection and/or quantification of a neuropathological aggregate of peptides or proteins in a tissue sample which tissue sample is obtained from a human or animal body, generally from the brain. The method involves the steps of (i) contacting the tissue sample with compounds of formula (I) (or the preferred formulae (II) to (VI)), including pharmaceutically active salt forms thereof, and (ii) detecting and/or quantifying the compounds which have bound to the sample. It will be understood that the sample is typically not returned into the body after the procedure. This method is e.g. suitable for a post-mortem assessment of a human or animal patient, including transgenic disease models that are characterized in the generation of such aggregates. Also in this context, the neuropathological aggregates of peptides or proteins are in particular β-amyloid (Aβ) aggregates, neurofibrillary tangles of tau (NFTs τ), α-synuclein aggregates, Prion ($^{Sc}$PrP), or Huntingtin, and the targets of most interest for the compounds of the invention are β-amyloid (Aβ) aggregates, neurofibrillary tangles of tau (NFTs τ), or α-synuclein aggregates. This method also allows the diagnosis of pathological conditions associated with the formation of neuropathological aggregates of peptides or proteins, in particular Alzheimer's disease (AD) and Alzheimer's disease related dementia, Parkinson's disease (PD) and Parkinson's disease related dementia, frontotemporal dementias (FTDP), Creutzfeldt-Jakob disease (CJD) and Creutzfeldt-Jakob disease related dementia, Huntington's disease (HD) and Huntington's disease related dementia, and Lewy body disease (DLB) and Lewy body disease related dementia. Conditions of most interest are Alzheimer's disease (AD) and Alzheimer's disease related dementia, Parkinson's disease (PD) and Parkinson's disease related dementia.

For an in vitro test of this type, the post-mortem brain homogenates with ND or the neuropeptidic aggregate samples to be tested can first be incubated with different concentrations of the compounds of the invention in presence or absence of a reference compound to allow them to bind to any neuropathological aggregates of peptides or proteins present in the sample. Compounds of the invention that have bound to the sample can be directly or indirectly detected e.g. after cell harvesting via nuclear medicine (scintillation or gamma measurements), fluorescence, optical methods, preferred nuclear medicine.

A noted above, the compounds of the invention that have bound to neuropathological aggregates of peptides or proteins in vitro or in vivo can be detected by a variety of methods. Most preferred among these are methods wherein a radiolabeled compound of the invention is administered to the human or animal for in vivo diagnosis, or contacted with the tissue sample in vitro. Preferred methods for in vivo diagnosis are PET or SPECT.

To that extent, radiolabeled compounds of formula (I) (or the preferred formulae (II) to (VI)), including a pharmaceutically active salt form thereof are particularly preferred which contain a radioisotope of an element contained in this compound.

As noted above, the radioisotope is contained in a substituent selected from those indicated in the above formulae, in particular in a substituent selected from $R^1$, $R^2$, $R^{1a}$, $R^{2a}$, substituents attached to $Ar^1$, $Ar^2$, $Ar^{1a}$, or $Ar^{2a}$, and $R^3$ to $R^8$, depending on the formula under consideration. Preferably, the substituent containing a radioisotope is selected from substituents attached to $Ar^1$, $Ar^2$, $Ar^{1a}$, or $Ar^{2a}$ and from $R^3$ to $R^8$. The substituent containing a radioisotope may be a single substituent in the compounds of formula (I) (or the preferred formulae (II) to (VI), including pharmaceutically active salt forms thereof), or two or more substituents may contain a radioisotope. Preferred radioisotopes that can be used for providing a radiolabeled compound are $^{18}F$, $^{11}C$, $^{3}H$, or $^{123}I$, $^{125}I$, $^{131}I$, more preferred are $^{18}F$, $^{123}I$ or $^{11}C$, and particularly preferred is $^{18}F$.

Thus, preferred compounds of formula (I) or (II), including a pharmaceutically active salt form thereof, for use in the present invention are radiolabeled compounds wherein at least one of the following requirements (i) to (iii) is met: (i) at least one of $R^1$ and $R^2$, if present, is $^{18}F$ or $^{123}I$, preferably $^{18}F$; (ii) at least one of $Ar^1$ and $Ar^2$ carries a substituent $^{18}F$ or $^{123}I$, preferably $^{18}F$; (iii) at least one of $Ar^1$ and $Ar^2$ carries a substituent comprising $^{18}F$, $^{123}I$, or $^{11}C$, preferably $^{18}F$ or $^{11}C$, and in particular $^{18}F$. More preferred as compounds for use in the present invention are radiolabeled compounds of formula (I) or (II), including a pharmaceutically active salt form thereof, wherein at least one of the requirements (ii) or (iii) is met.

Preferred compounds of formula (III) or (IV), including a pharmaceutically active salt form thereof, for use in the present invention are radiolabeled compounds wherein at least one of the following requirements (i) to (iii) is met: (i) at least one of $R^{1a}$ and $R^{2a}$, if present, is $^{18}F$ or $^{123}I$, preferably $^{18}F$; (ii) at least one of $Ar^{1a}$ and $Ar^{2a}$ carries a substituent $^{18}F$ or $^{123}I$, preferably $^{18}F$; (iii) at least one of $Ar^{1a}$ and $Ar^{2a}$ carries a substituent comprising 18F, $^{123}I$, or $^{11}C$, preferably $^{18}F$ or $^{11}C$, and in particular $^{18}F$. More preferred as compounds for use in the present invention are radiolabeled compounds of formula (III) or (IV) including a pharmaceutically active salt form thereof, wherein at least one of the requirements (ii) or (iii) is met.

Preferred compounds of formula (V) or (VI), including a pharmaceutically active salt form thereof, for use in the present invention are radiolabeled compounds wherein at least one of the following requirements (i) to (iii) is met: (i) at least one of $R^{1a}$ and $R^{2a}$, if present, is $^{18}F$ or $^{123}I$, preferably $^{18}F$; (ii) at least one of $R^3$ to $R^8$ is a substituent $^{18}F$ or $^{123}I$, preferably $^{18}F$; (iii) at least one of $R^3$ to $R^8$ is a substituent comprising $^{18}F$, $^{123}I$, or $^{11}C$, preferably $^{18}F$ or $^{11}C$, and in particular $^{18}F$. More preferred as compounds for use in the present invention are radiolabeled compounds of formula (V) or (VI) including a pharmaceutically active salt form thereof, wherein at least one of the requirements (ii) or (iii) is met.

As radiolabeled tracers or imaging agents, the compounds of the invention provide the possibility of n.c.a (no carrier added) radiolabeling, especially with $^{18}F$, and thus for a more convenient and simple design of automated processes for GMP-production of $^{18}F$-radiopharmaceuticals in clinical settings.

Preferred radiolabeled compounds of the present invention which contain a $^{18}F$ atom can be provided, e.g., via nucleophilic substitution, including aromatic nucleophilic substitution, of another substituent (i.e. a suitable leaving group) attached to a primary, secondary or aromatic carbon atom. Suitable procedures for radiofluorination are described, e.g. in Yousefi et al., 2011.

Thus, as radiolabeled compounds of the present invention which contain a $^{18}F$ atom, compounds are preferred wherein the $^{18}F$ atom is attached as a substituent to $Ar^1$, $Ar^2$, $Ar^{1a}$, or $Ar^{2a}$, or wherein one of $R^3$ to $R^8$ is a $^{18}F$ atom. Further preferred compounds of the present invention wherein a $^{18}F$ atom is contained are those wherein the $^{18}F$ is part of a haloalkyl group, which may be a substituent on one or both of the two rings $Ar^1$ and $Ar^2$ in the compounds of formula (I), or on the corresponding rings in the compounds of formulae (II) to (VI), or which may be a haloalkyl group forming part of another substituent on one or both of the two rings $Ar^1$ and $Ar^2$ in the compounds of formula (I), or on the corresponding rings in the compounds of formulae (II) to (VI), such as —(O—CH$_2$—CH$_2$)$_o$—F, wherein o is defined as above. It is particularly preferred that the $^{18}F$ is part of a fluoromethyl group CH$_2$$^{18}F$, which may also form part of another substituent.

Preferred radiolabeled compounds of the present invention which contain a $^{11}C$ atom can be provided, e.g., via a typical substitution at a primary or secondary amine, or at a hydroxyl group, e.g. using [$^{11}C$]CH$_3$I or [$^{11}C$]CH$_3$OTf (with OTf being a trifluoromethanesulfonate) as a reactant. Suitable procedures for radiofluorination are described, e.g. in Yousefi et al., 2011.

Thus, as radiolabeled compounds of the present invention which contain a $^{11}C$ atom, compounds are preferred wherein the $^{11}C$ atom forms part of a [$^{11}C$]CH$_3$O— group ($^{11}C$ methoxy group) which may be a substituent on one or both of the two rings $Ar^1$ and $Ar^2$ in the compounds of formula (I), or on the corresponding rings in the compounds of formulae (II) to (VI) or which may be a methoxy group forming part of another substituent. Further preferred compounds which contain a $^{11}C$ atom are those which contain a secondary or tertiary alkylamino group as a substituent, wherein the nitrogen atom carries a [$^{11}C$]CH$_3$—($^{11}C$ methyl) group.

A further aspect of the invention is directed to a diagnostic composition comprising a radiolabeled compound of any of formulae (I) to (VI) or a pharmaceutically active salt form thereof, optionally together with a pharmaceutically acceptable carrier, diluent and/or excipient. Preferred as carrier is water, PBS buffer or an isotonic aqueous solution.

As noted above, a radiolabeled compound is one which contains a radioisotope of an element contained in this compound. As also noted above, the radioisotope is contained in a substituent selected from those indicated in the above formulae, in particular in a substituent selected from $R^1$, $R^2$, $R^{1a}$, $R^{2a}$, substituents attached to $Ar^1$, $Ar^2$, $Ar^{1a}$, $Ar^{2a}$, and $R^3$ to $R^8$, depending on the formula under consideration. Preferably, the substituent containing a radioisotope is selected from substituents bound to $Ar^1$, $Ar^2$, $Ar^{1a}$, $Ar^{2a}$ and from $R^3$ to $R^8$. The substituent containing a radioisotope may be a single substituent in the compounds of formula (I) (or the preferred formulae (II) to (VI)), including pharmaceutically active salt forms thereof, or two or more substituents may contain a radioisotope. It will be understood that the information provided above with respect to the preferred radioisotopes and the preferred positions thereof in the compounds of formula (I) (or the preferred formulae (II) to (VI)), including pharmaceutically active salt forms thereof, provided above also applies with respect to the diagnostic composition comprising a radiolabeled compound of this aspect of the invention.

Finally, the invention provides a process for the provision of a radiolabeled compound of formula (I) or a pharmaceutically acceptable salt form thereof, said process comprising the conversion of a non-radiolabeled compound of formula (I) as a precursor compound to a radiolabeled compound via reaction of the non-radiolabeled precursor compound with a reactant containing a radioisotope. It will be understood that the information provided above with respect to the preferred radioisotopes and the preferred positions thereof in the compounds of formula (I) also applies with respect to the process for the provision of a radiolabeled compound of this aspect of the invention. Moreover, it will be understood that the process is also applicable to the preferred compounds of formulae (II) to (VI), and to pharmaceutically acceptable salt forms of the compounds of formulae (I) to (VI).

Similarly, the present invention encompasses the use of a non-radiolabeled compound of formula (I) or a pharmaceutically acceptable salt form thereof as a precursor for a radiolabeled compound of formula (I), including pharmaceutically active salt forms thereof). Also this aspect of the invention is applicable to the preferred compounds of formulae (II) to (VI), and to pharmaceutically acceptable salt forms of the compounds of formulae (II) to (VI).

EXAMPLES

A library of bithiazoles was prepared using available building blocks (e.g. acyl bromides or acyl chlorides) using one step or two-step synthesis. Two-step synthesis of the bisthiazoles was carried out in DMF at room temperature (Mikhailenko et al., Mol. Cryst. Liq. Cryst., Vol. 542: pp. 115/[637]-122/[644], 2011):

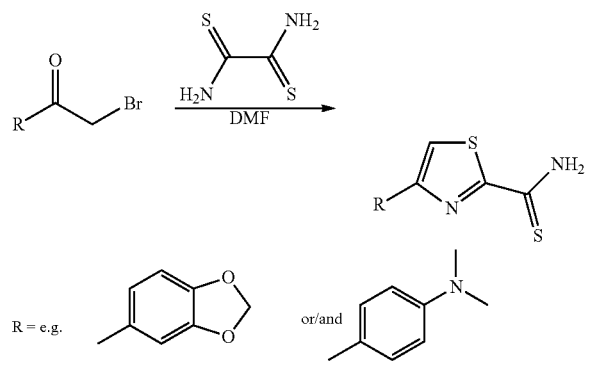

For the preparation of asymmetric bithiazoles, the resulting product may be reacted with a different acyl bromide in line with the following scheme:

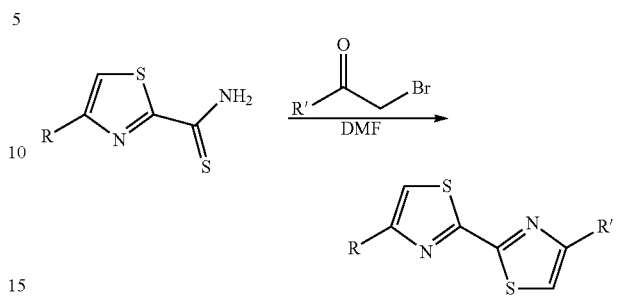

A one-step combinatorial approach for synthesis of the bithiazoles was performed in ethanol at reflux temperature:

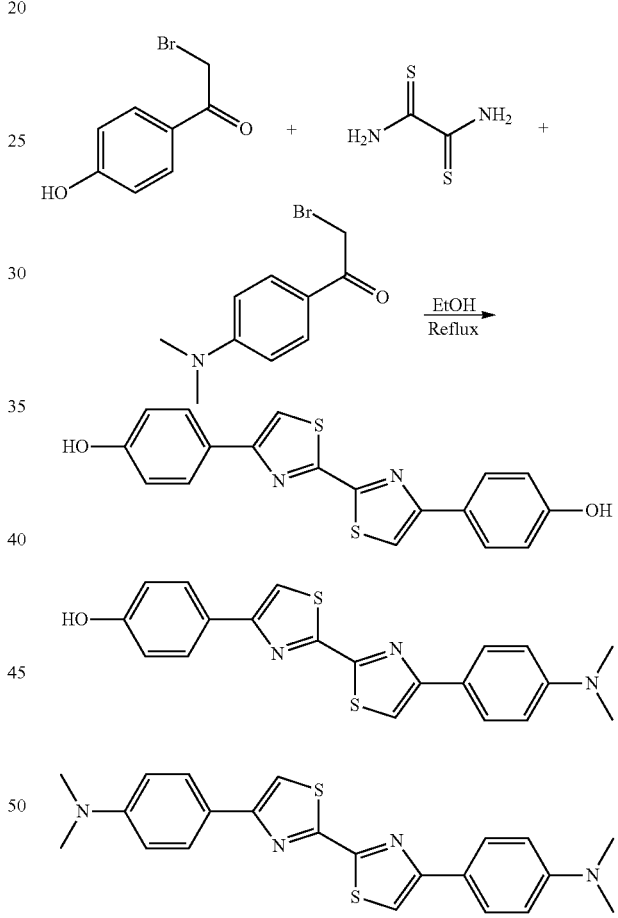

The mixture of three possible products was purified by means of flash chromatography or preparative HPLC. Exemplary compounds obtained following these routes are listed in the following:

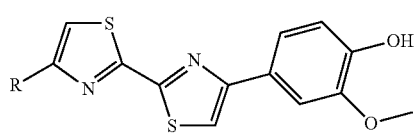

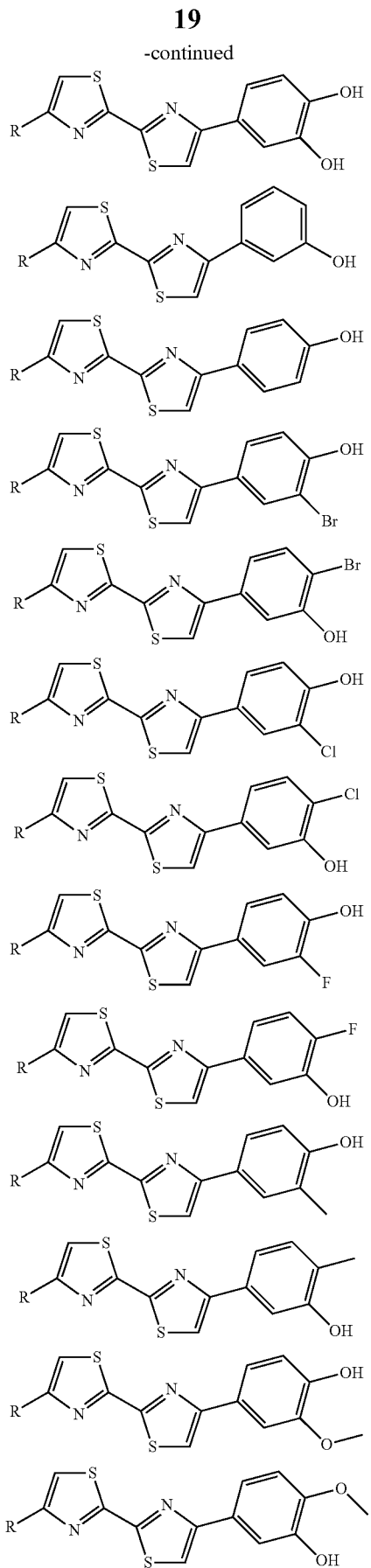

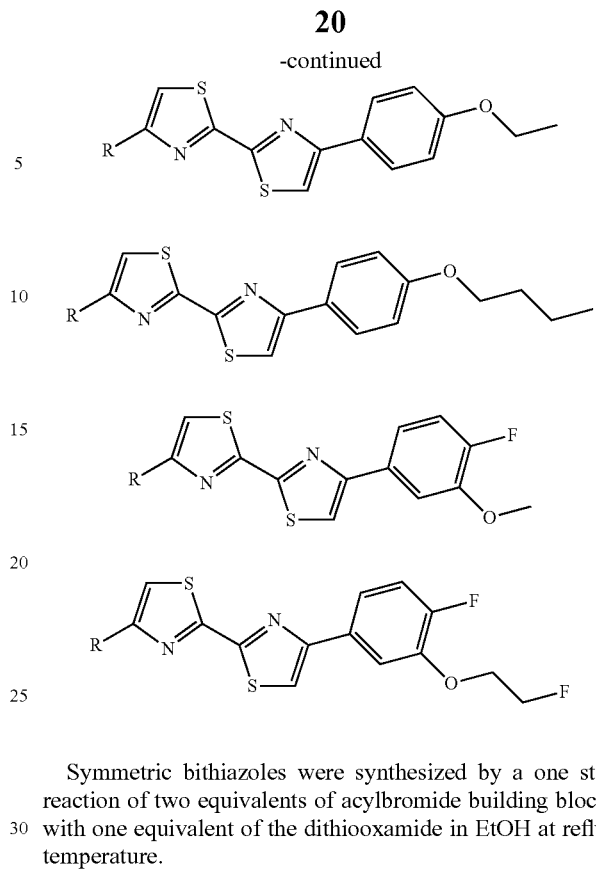

Symmetric bithiazoles were synthesized by a one step reaction of two equivalents of acylbromide building blocks with one equivalent of the dithiooxamide in EtOH at reflux temperature.

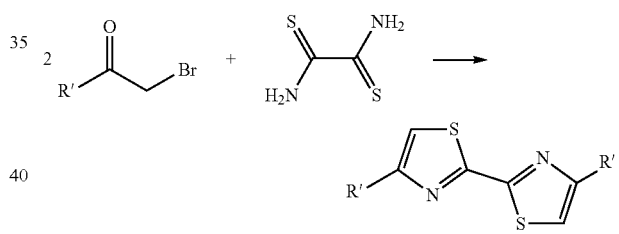

All isolated intermediates and products were confirmed by mass spectrometry, $^1$H-NMR and selected compound also confirmed by $^{13}$C-NMR spectroscopy.

Saturation and competition binding assays of compounds in this invention towards synthetic amyloid peptides, human tau-441 recombinant and human α-synuclein recombinant aggregate (fibrils) were performed similar to previously reported assays (Manook et al. 2012 and Yousefi et al. 2011) and adapted to the change of peptides and label. Aggregates sample was deployed on 96-well cell culture plates (Greiner Bio-One, Germany) to a final reaction volume of 280 mL per well using 8-channel electronic pipettes (Mettler Toledo, Germany) giving 12-24 octuples of data points per sample. Bound and free fractions were separated by vacuum filtration through polyethyleneimine-pretreated GF/B glass filtermats using a semi-automated Harvester 96 Mach II M (Tomtec, USA). Filters were cut and retained radioactivity determined using an automatic NaI(Tl) well-type γ-detector (Wallac 1480-011 Automatic Gamma Counter, PerkinElmer, USA). Data were processed and analyzed using GraphPad Prism 6.0 (GraphPad Software, USA). The results are shown in the following tables:

TABLE 1

Data on selected example compounds' $A\beta_{1-40}$, $A\beta_{1-42}$ $\tau$, $\alpha$-Syn affinities

| Compound | Structure | ClogP | % Inhibition of [$^3$H]PiB at 100 nM $A\beta_{1-40}$ | $A\beta_{1-42}$ | T | Affinity Ki (nM) $\alpha$-syn | $A\beta_{1-40}$ | $A\beta_{1-42}$ | Potential Use: Targeting of |
|---|---|---|---|---|---|---|---|---|---|
| 1 | (dimethylamino-phenyl)-thiazole-thiazole-(4-hydroxyphenyl) | 5.22 | 94 ± 0 | 88 ± 1 | >1000 | >1000 | 4 | 6 | A$\beta$ |
| 2 | (benzodioxole)-thiazole-thiazole-(3-hydroxy-4-methoxyphenyl) | 4.79 | 81 ± 2 | 86 ± 1 | 12 | 9 | 10 | 7 | A$\beta$, $\alpha$-syn, $\tau$-aggregates (PAN-ligand) |
| 3 | (benzodioxole)-thiazole-thiazole-(3-fluoro-4-methoxyphenyl) | 5.47 | 22 ± 1 | 45 ± 2 | >1000 | 3 | — | 382 | $\alpha$-syn |
| 4 | (benzodioxole)-thiazole-thiazole-(4-ethoxyphenyl) | 5.95 | 11 ± 2 | 45 ± 2 | 558 | 10 | — | 386 | $\alpha$-syn |
| 5 | (3-fluoro-4-methoxyphenyl)-thiazole-thiazole-(4-butoxyphenyl) | 5.98 | 11 ± 0 | 45 ± 1 | >1000 | 328 | — | 380 | A$\beta$, $\alpha$-syn aggregates low binding site |
| 6 | (4-methoxyphenyl)-thiazole-thiazole-(4-ethoxyphenyl) | 5.96 | 22 ± 1 | 30 ± 1 | >1000 | 371 | — | — | $\alpha$-syn aggregates low binding site |

Example compound 2 binds to β-amyloids, NFT τ and synuclein aggregates with in vitro affinity of 7-12 nM (Ki, see table 1). Specificity studies with ex vivo and in vitro validation on APP/PS1 (Willuweit et al., 2009, Manook et al., 2012) and a APP/PS1-tau triple tg mouse model of AD brain confirmed specific binding of compound 2 to Aβ and NFT (FIG. 2-4).

In vitro staining experiments of compound 2 on APP/PS1 tg mouse brain showed specific binding to β-amyloids (FIG. 2).

The biodistribution study (following the procedure previously described (Yousefi et al., 2011)) results confirmed that compound [$^{11}$C]2 as a representative compound for the brain uptake behaviour of the compounds of formula (I), crosses the blood brain barrier and clears from brain in 30 min p.i. fast (in wt Balb-C mice) which is a very important property of a CNS tracer.

These results suggest by further modification of functional groups and introduction of F-18 with physical half life of 110 min even superior compounds could be prepared (Table 2).

TABLE 2

Library of the compounds based of bithiazole were synthesized, the table indicates their logP (octanol/PBS), mass spectrometry and in vitro selectivity.

| Compound | log P (Octanol/PBS) | MS [M + 1] amu | Potential Use: Targeting of |
|---|---|---|---|
| 7 | 3.2 | 412.1 | Aβ |
| 8 | 2.1 | 443.2 | PAN |
| 9 | 1.9 | 487.1 | PAN |
| 10 | 2.6 | 427.1 | α-syn |
| 11 | 2.5 | 471.2 | α-syn |
| 12 | 2.0 | 485.2 | Aβ |
| 13 | 2.6 | 470.2 | Aβ |

TABLE 2-continued

Library of the compounds based of bithiazole were synthesized, the table indicates their logP (octanol/PBS), mass spectrometry and in vitro selectivity.

| Compound | log P (Octanol/PBS) | MS [M + 1] amu | Potential Use: Targeting of |
|---|---|---|---|
| 14 | 1.9 | 443.1 | The low binding site of Aβ |
| 15 | 2.6 | 413.1 | α-syn |
| 16 | 1.1 | 475.1 | PAN |
| 17 | 1.8 | 487.2 | The low binding site of Aβ |
| 18 | 2.3 | 515.2 | α-syn |
| 19 | 2.4 | 513.2 | Aβ |
| 20 | 1.9 | 381.3 | Aβ |

TABLE 2-continued

Library of the compounds based of bithiazole were synthesized, the table indicates their logP (octanol/PBS), mass spectrometry and in vitro selectivity.

| Compound | | log P (Octanol/ PBS) | MS [M + 1] amu | Potential Use: Targeting of |
|---|---|---|---|---|
| 21 | 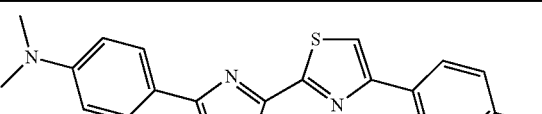 | 2.1 | 383.2 | Aβ |
| 22 | | 3.2 | 450.1 | α-syn |
| 23 | | 2.9 | 419.1 | PAN |

TABLE 3

Data on compounds 20-23 affinities

| Compound | | logP | % Inhibition of [³H]PiB at 100 nM | | Affinity Ki (nM) | | | Potential Use: Targeting of |
| | | | Aβ$_{1-40}$ | Aβ$_{1-42}$ | τ | α-syn | Aβ$_{1-40}$ | Aβ$_{1-42}$ | |
|---|---|---|---|---|---|---|---|---|---|
| 20 | 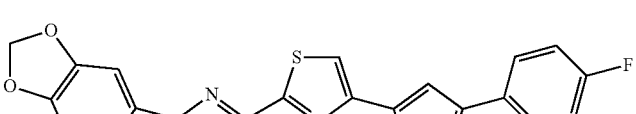 | 1.9 | 90 ± 0 | 89 ± 1 | >1000 | >1000 | 5 | 6 | Aβ |
| 21 | | 2.1 | 89 ± 2 | 88 ± 1 | >1000 | >1000 | 6 | 6 | Aβ |
| 22 | | 3.2 | 20 ± 1 | 35 ± 2 | >1000 | 6 | >500 | 492 | α-syn |
| 23 | 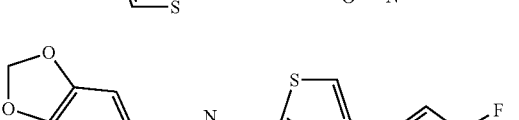 | 2.9 | 87 ± 2 | 86 ± 1 | 10 | 7 | 9 | 10 | PAN |

Lipophilicity of CNS tracers plays an important role on blood brain barrier (BBB) and neuronal cells uptake. Therefore a library of $^{18}$F-bithiazoles with high binding affinity towards $A\beta_{1\text{-}40}$, $A\beta_{1\text{-}42}$ τ, α-Syn were synthesized and log P (octanol/PBS) of these compounds measured (Table 2). The log P values were between 1.1-3.2. This suggests that all compounds are crossing BBB and compounds with log P 1.9-2.6 penetrate cell membrane and reach intercellular targets.

LIST OF REFERENCES

Agdeppa E D, Kepe V, Liu J, Flores-Torres S, Satyamurthy N, Petric A, Cole G M, Small G W, Huang S C, Barrio J R (2001) Binding characteristics of radiofluorinated 6-dialkylamino-2-naphthylethylidene derivatives as positron emission tomography imaging probes for beta-amyloid plaques in Alzheimer's disease. The Journal of neuroscience: the official journal of the Society for Neuroscience 21:RC189.

Asuni A A, Boutajangout A, Quartermain D, Sigurdsson E M (2007) Immunotherapy targeting pathological tau conformers in a tangle mouse model reduces brain pathology with associated functional improvements. The Journal of neuroscience: the official journal of the Society for Neuroscience 27:9115-9129.

Bagchi D P, Yu L, Perlmutter J S, Xu J, Mach R H, Tu Z, Kotzbauer P T (2013) Binding of the radioligand SIL23 to alpha-synuclein fibrils in Parkinson disease brain tissue establishes feasibility and screening approaches for developing a Parkinson disease imaging agent. PloS one 8:e55031.

Baksalerska-Pazera M, Niewiadomska G (2002) [Structure and role of the tau protein]. Postepy biochemii 48:287-295.

Barghorn S, Davies P, Mandelkow E (2004) Tau paired helical filaments from Alzheimer's disease brain and assembled in vitro are based on beta-structure in the core domain. Biochemistry 43:1694-1703.

Berriman J, Serpell L C, Oberg K A, Fink A L, Goedert M, Crowther R A (2003) Tau filaments from human brain and from in vitro assembly of recombinant protein show cross-beta structure. Proceedings of the National Academy of Sciences of the United States of America 100:9034-9038.

Bierer L M, Hof P R, Purohit D P, Carlin L, Schmeidler J, Davis K L, Perl D P (1995) Neocortical neurofibrillary tangles correlate with dementia severity in Alzheimer's disease. Archives of neurology 52:81-88.

Bierer L M, Perl D P, Haroutunian V, Mohs R C, Davis K L (1990) Neurofibrillary tangles, Alzheimer's disease and Lewy bodies. Lancet 335:163.

Chang E, Honson N S, Bandyopadhyay B, Funk K E, Jensen J R, Kim S, Naphade S, Kuret J (2009) Modulation and detection of tau aggregation with small-molecule ligands. Current Alzheimer research 6:409-414.

Chien D T, Bahri S, Szardenings A K, Walsh J C, Mu F R, Su M Y, Shankle W R, Elizarov A, Kolb H C (2013) Early Clinical PET Imaging Results with the Novel PHF-Tau Radioligand [F-18]-T807. J Alzheimers Dis 34:457-468.

Couchie D, Mavilia C, Georgieff I S, Liem R K, Shelanski M L, Nunez J (1992) Primary structure of high molecular weight tau present in the peripheral nervous system. Proceedings of the National Academy of Sciences of the United States of America 89:4378-4381.

Diaz-Ruiz C, Wang J, Ksiezak-Reding H, Ho L, Qian X, Humala N, Thomas S, Martinez-Martin P, Pasinetti G M (2009) Role of Hypertension in Aggravating Abeta Neuropathology of AD Type and Tau-Mediated Motor Impairment. Cardiovascular psychiatry and neurology 2009:107286.

Dickson D W (2005) Required techniques and useful molecular markers in the neuropathologic diagnosis of neurodegenerative diseases. Acta neuropathologica 109:14-24.

Drzezga A (2008) Basic pathologies of neurodegenerative dementias and their relevance for state-of-the-art molecular imaging studies. European journal of nuclear medicine and molecular imaging 35 Suppl 1:S4-11.

Fowler D M, Kelly J W (2009) Aggregating knowledge about prions and amyloid. Cell 137:20-22.

Fowler D M, Kelly J W (2012) Functional amyloidogenesis and cytotoxicity-insights into biology and pathology. PLoS biology 10:e1001459.

Fowler D M, Koulov A V, Balch W E, Kelly J W (2007) Functional amyloid—from bacteria to humans. Trends in biochemical sciences 32:217-224.

Friedhoff P, von Bergen M, Mandelkow E M, Mandelkow E (2000) Structure of tau protein and assembly into paired helical filaments. Biochimica et biophysica acta 1502:122-132.

Goedert M (2001) Alpha-synuclein and neurodegenerative diseases. Nature reviews Neuroscience 2:492-501.

Goedert M, Spillantini M G, Del Tredici K, Braak H (2013) 100 years of Lewy pathology. Nature reviews Neurology 9:13-24.

Gotz J, Ittner A, Ittner L M (2012) Tau-targeted treatment strategies in Alzheimer's disease. British journal of pharmacology 165:1246-1259.

Gotz J, Inner L M (2008) Animal models of Alzheimer's disease and frontotemporal dementia. Nature reviews Neuroscience 9:532-544.

Ikonomovic M D, Abrahamson E E, Isanski B A, Debnath M L, Mathis C A, Dekosky S T, Klunk W E (2006) X-34 labeling of abnormal protein aggregates during the progression of Alzheimer's disease. Methods in enzymology 412:123-144.

Inouye H, Sharma D, Goux W J, Kirschner D A (2006) Structure of core domain of fibril-forming PHF/Tau fragments. Biophysical journal 90:1774-1789.

Iqbal K, Liu F, Gong C X, Alonso Adel C, Grundke-Iqbal I (2009) Mechanisms of tau-induced neurodegeneration. Acta neuropathologica 118:53-69.

Inner A, Ke Y D, van Eersel J, Gladbach A, Gotz J, Ittner L M (2011) Brief update on different roles of tau in neurodegeneration. IUBMB life 63:495-502.

Kosik K S, Kowall N W, McKee A (1989) Along the way to a neurofibrillary tangle: a look at the structure of tau. Annals of medicine 21:109-112.

Kotzbauer P T, Trojanowsk J Q, Lee V M (2001) Lewy body pathology in Alzheimer's disease. Journal of molecular neuroscience: MN 17:225-232.

Landau S M, Breault C, Joshi A D, Pontecorvo M, Mathis C A, Jagust W J, Mintun M A, Alzheimer's Disease Neuroimaging I (2013) Amyloid-beta imaging with Pittsburgh compound B and florbetapir: comparing radiotracers and quantification methods. Journal of nuclear medicine: official publication, Society of Nuclear Medicine 54:70-77.

Li L, von Bergen M, Mandelkow E M, Mandelkow E (2002) Structure, stability, and aggregation of paired helical filaments from tau protein and FTDP-17 mutants probed by tryptophan scanning mutagenesis. The Journal of biological chemistry 277:41390-41400.

Lockhart A, Lamb J R, Osredkar T, Sue L I, Joyce J N, Ye L, Libri V, Leppert D, Beach T G (2007) PIB is a non-specific imaging marker of amyloid-beta (Abeta) peptide-related cerebral amyloidosis. Brain: a journal of neurology 130:2607-2615.

Love S (2005) Neuropathological investigation of dementia: a guide for neurologists. Journal of neurology, neurosurgery, and psychiatry 76 Suppl 5:v8-14.

Manook A, Yousefi B H, Willuweit A, Platzer S, Reder S, Voss A, Huisman M, Settles M, Neff F, Velden J, Schoor M, von der Kammer H, Wester H J, Schwaiger M, Henriksen G, Drzezga A (2012) Small-animal PET imaging of amyloid-beta plaques with [11C]PiB and its multimodal validation in an APP/PS1 mouse model of Alzheimer's disease. PloS one 7:e31310.

Mudher A, Lovestone S (2002) Alzheimer's disease-do tauists and baptists finally shake hands? Trends in neurosciences 25:22-26.

Mukrasch M D, Biernat J, von Bergen M, Griesinger C, Mandelkow E, Zweckstetter M (2005) Sites of tau important for aggregation populate {beta}-structure and bind to microtubules and polyanions. The Journal of biological chemistry 280:24978-24986.

Ojida A, Sakamoto T, Inoue M A, Fujishima S H, Lippens G, Hamachi I (2009) Fluorescent BODIPY-based Zn(II) complex as a molecular probe for selective detection of neurofibrillary tangles in the brains of Alzheimer's disease patients. Journal of the American Chemical Society 131:6543-6548.

Okamura N, Suemoto T, Furumoto S, Suzuki M, Shimadzu H, Akatsu H, Yamamoto T, Fujiwara H, Nemoto M, Maruyama M, Arai H, Yanai K, Sawada T, Kudo Y (2005) Quinoline and benzimidazole derivatives: candidate probes for in vivo imaging of tau pathology in Alzheimer's disease. The Journal of neuroscience: the official journal of the Society for Neuroscience 25:10857-10862.

Okamura N, Suemoto T, Shiomitsu T, Suzuki M, Shimadzu H, Akatsu H, Yamamoto T, Arai H, Sasaki H, Yanai K, Staufenbiel M, Kudo Y, Sawada T (2004) A novel imaging probe for in vivo detection of neuritic and diffuse amyloid plaques in the brain. Journal of molecular neuroscience: MN 24:247-255.

Ossenkoppele R, Tolboom N, Foster-Dingley J C, Adriaanse S F, Boellaard R, Yaqub M, Windhorst A D, Barkhof F, Lammertsma A A, Scheltens P, van der Flier W M, van Berckel B N (2012) Longitudinal imaging of Alzheimer pathology using [11C]PIB, [18F]FDDNP and [18F]FDG PET. European journal of nuclear medicine and molecular imaging 39:990-1000.

Petrou M, Bohnen N I, Muller M L, Koeppe R A, Albin R L, Frey K A (2012) Abeta-amyloid deposition in patients with Parkinson disease at risk for development of dementia. Neurology 79:1161-1167.

Rambaran R N, Serpell L C (2008) Amyloid fibrils: abnormal protein assembly. Prion 2:112-117.

Schweers O, Schonbrunn-Hanebeck E, Marx A, Mandelkow E (1994) Structural studies of tau protein and Alzheimer paired helical filaments show no evidence for beta-structure. The Journal of biological chemistry 269:24290-24297.

Serpell L C, Berriman J, Jakes R, Goedert M, Crowther R A (2000) Fiber diffraction of synthetic alpha-synuclein filaments shows amyloid-like cross-beta conformation. Proceedings of the National Academy of Sciences of the United States of America 97:4897-4902.

Sevcik J, Skrabana R, Dvorsky R, Csokova N, Iqbal K, Novak M (2007) X-ray structure of the PHF core C-terminus: insight into the folding of the intrinsically disordered protein tau in Alzheimer's disease. FEBS letters 581:5872-5878.

Shoghi-Jadid K, Small G W, Agdeppa E D, Kepe V, Ercoli L M, Siddarth P, Read S, Satyamurthy N, Petric A, Huang S C, Barrio J R (2002) Localization of neurofibrillary tangles and beta-amyloid plaques in the brains of living patients with Alzheimer disease. The American journal of geriatric psychiatry: official journal of the American Association for Geriatric Psychiatry 10:24-35.

Small G W, Agdeppa E D, Kepe V, Satyamurthy N, Huang S C, Barrio J R (2002) In vivo brain imaging of tangle burden in humans. Journal of molecular neuroscience: MN 19:323-327.

Song P J, Bernard S, Sarradin P, Vergote J, Barc C, Chalon S, Kung M P, Kung H F, Guilloteau D (2008) IMPY, a potential beta-amyloid imaging probe for detection of prion deposits in scrapie-infected mice. Nuclear medicine and biology 35:197-201.

Spillantini M G, Tolnay M, Love S, Goedert M (1999) Microtubule-associated protein tau, heparan sulphate and alpha-synuclein in several neurodegenerative diseases with dementia. Acta neuropathologica 97:585-594.

Styren S D, Hamilton R L, Styren G C, Klunk W E (2000) X-34, a fluorescent derivative of Congo red: a novel histochemical stain for Alzheimer's disease pathology. The journal of histochemistry and cytochemistry: official journal of the Histochemistry Society 48:1223-1232.

Suemoto T, Okamura N, Shiomitsu T, Suzuki M, Shimadzu H, Akatsu H, Yamamoto T, Kudo Y, Sawada T (2004) In vivo labeling of amyloid with BF-108. Neuroscience research 48:65-74.

Tolboom N, van der Flier W M, Yaqub M, Koene T, Boellaard R, Windhorst A D, Scheltens P, Lammertsma A A, van Berckel B N (2009a) Differential association of [11C]PIB and [18F]FDDNP binding with cognitive impairment. Neurology 73:2079-2085.

Tolboom N, Yaqub M, van der Flier W M, Boellaard R, Luurtsema G, Windhorst A D, Barkhof F, Scheltens P, Lammertsma A A, van Berckel B N (2009b) Detection of Alzheimer pathology in vivo using both 11C-PIB and 18F-FDDNP PET. Journal of nuclear medicine: official publication, Society of Nuclear Medicine 50:191-197.

Willuweit A, Velden J, Godemann R, Manook A, Jetzek F, Tintrup H, Kauselmann G, Zevnik B, Henriksen G, Drzezga A, Pohlner J, Schoor M, Kemp J A, von der Kammer H (2009) Early-onset and robust amyloid pathology in a new homozygous mouse model of Alzheimer's disease. PloS one 4:e7931.

Ye L, Velasco A, Fraser G, Beach T G, Sue L, Osredkar T, Libri V, Spillantini M G, Goedert M, Lockhart A (2008) In vitro high affinity alpha-synuclein binding sites for the amyloid imaging agent PIB are not matched by binding to Lewy bodies in postmortem human brain. Journal of neurochemistry 105:1428-1437.

Yousefi B H, Manook A, Drzezga A, von Reutern B, Schwaiger M, Wester H J, Henriksen G (2011) Synthesis and evaluation of 11C-labeled imidazo[2,1-b]benzothiazoles (IBTs) as PET tracers for imaging beta-amyloid plaques in Alzheimer's disease. Journal of medicinal chemistry 54:949-956.

Yu L, Cui J, Padakanti P K, Engel L, Bagchi D P, Kotzbauer P T, Tu Z (2012) Synthesis and in vitro evaluation of alpha-synuclein ligands. Bioorganic & medicinal chemistry 20:4625-4634.

Figure 1:
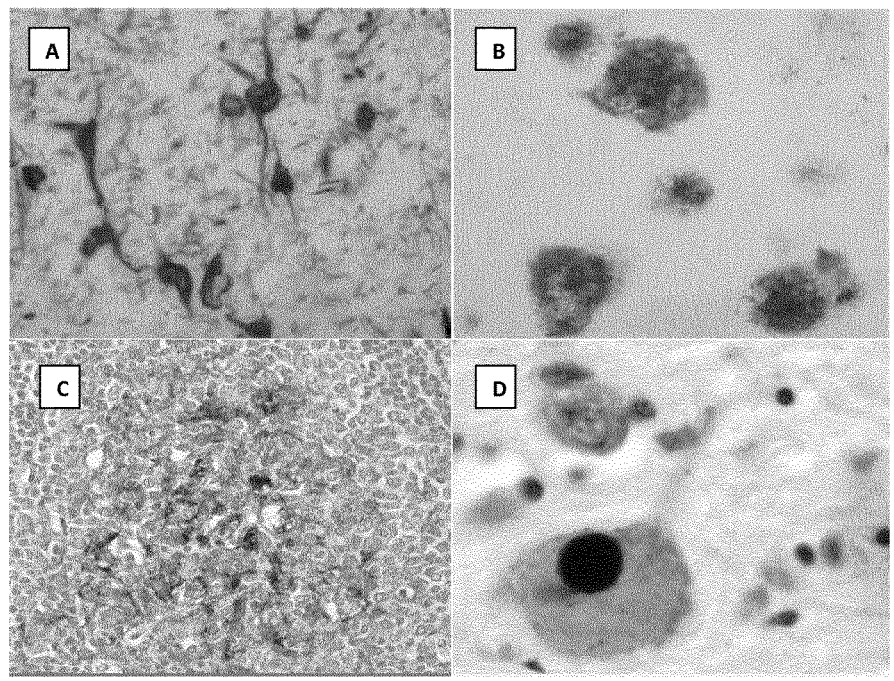
FIG. 1 shows images of neurofibrillary tangles (A) and β-Amyloid plaques (B) post-mortem staining in a patient with AD, abnormal $^{SC}$PrP immunoreactivity in a submucosal lymphoid aggregate in variant Creutzfeldt-Jakob disease rectum (C), positive α-Synuclein staining of a Lewy body in a patient with Parkinson's disease (D).
Figure 2:
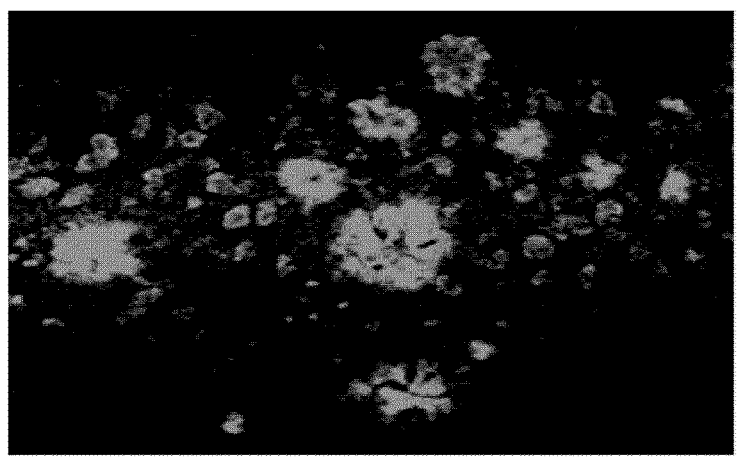
FIG. 2 shows an image of a APP/PS1 mouse model of AD brain (24 month old) stained with 1% solution of compound 2 that confirms the compound targets Aβ in the mouse model.
Figure 3:
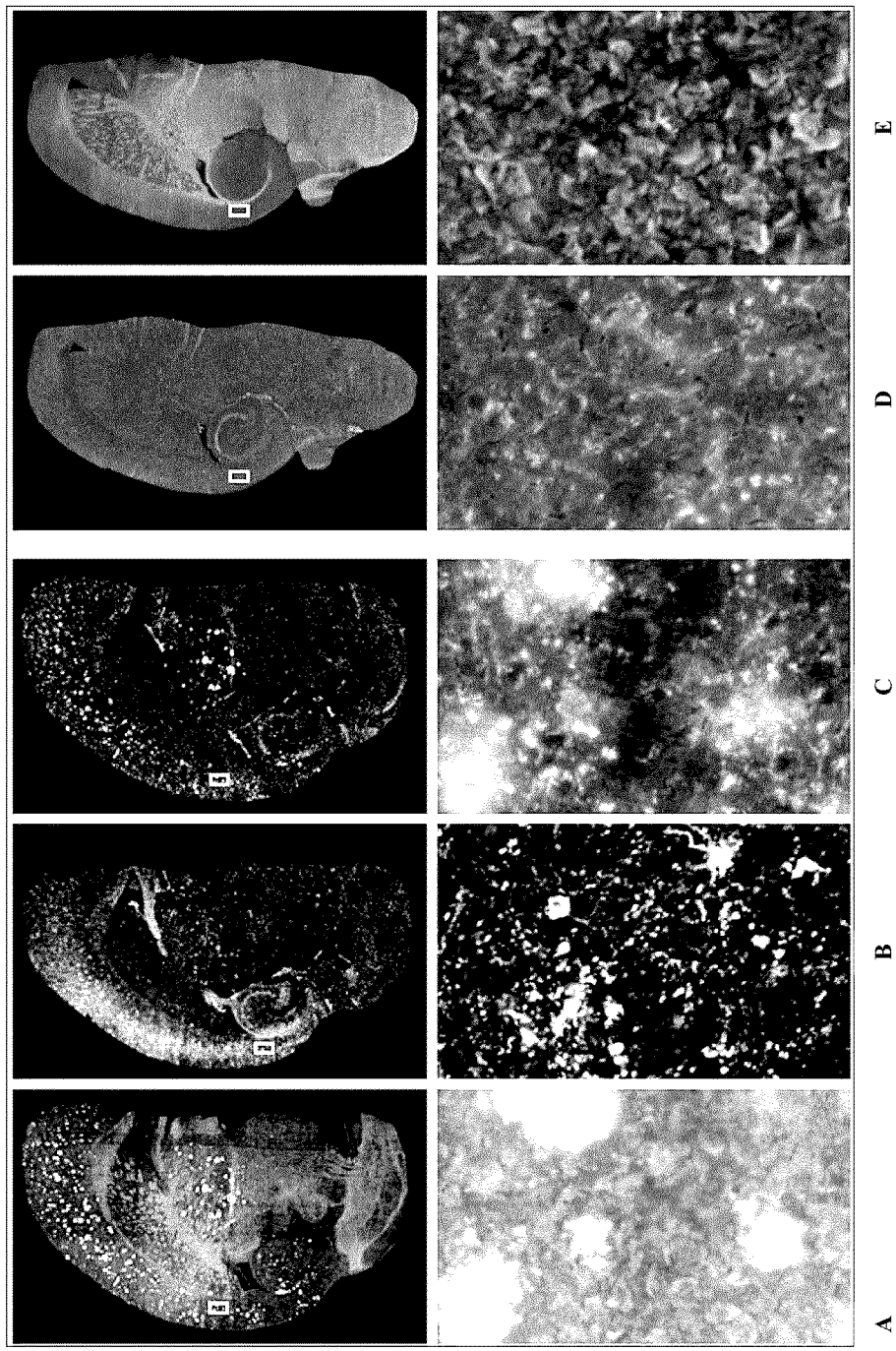
FIG. 3 shows images of ex vivo APP/PS1-tau triple transgenic mouse model of AD (images A-C) and age matched control mouse (images D, E) brain (24 month old) 45 min p.i., 0.6 mg of compound 2 (in DMSO), cross-validated with thioflavin S (images A and E) and tau Antibody AT8 stain of a neighboring slice (images B) that confirms the compound targets Aβ and NFT in the mouse model. Magnification of cortical region proved the compound uptakes on Aβ and NFT in the mouse model.
Figure 4:
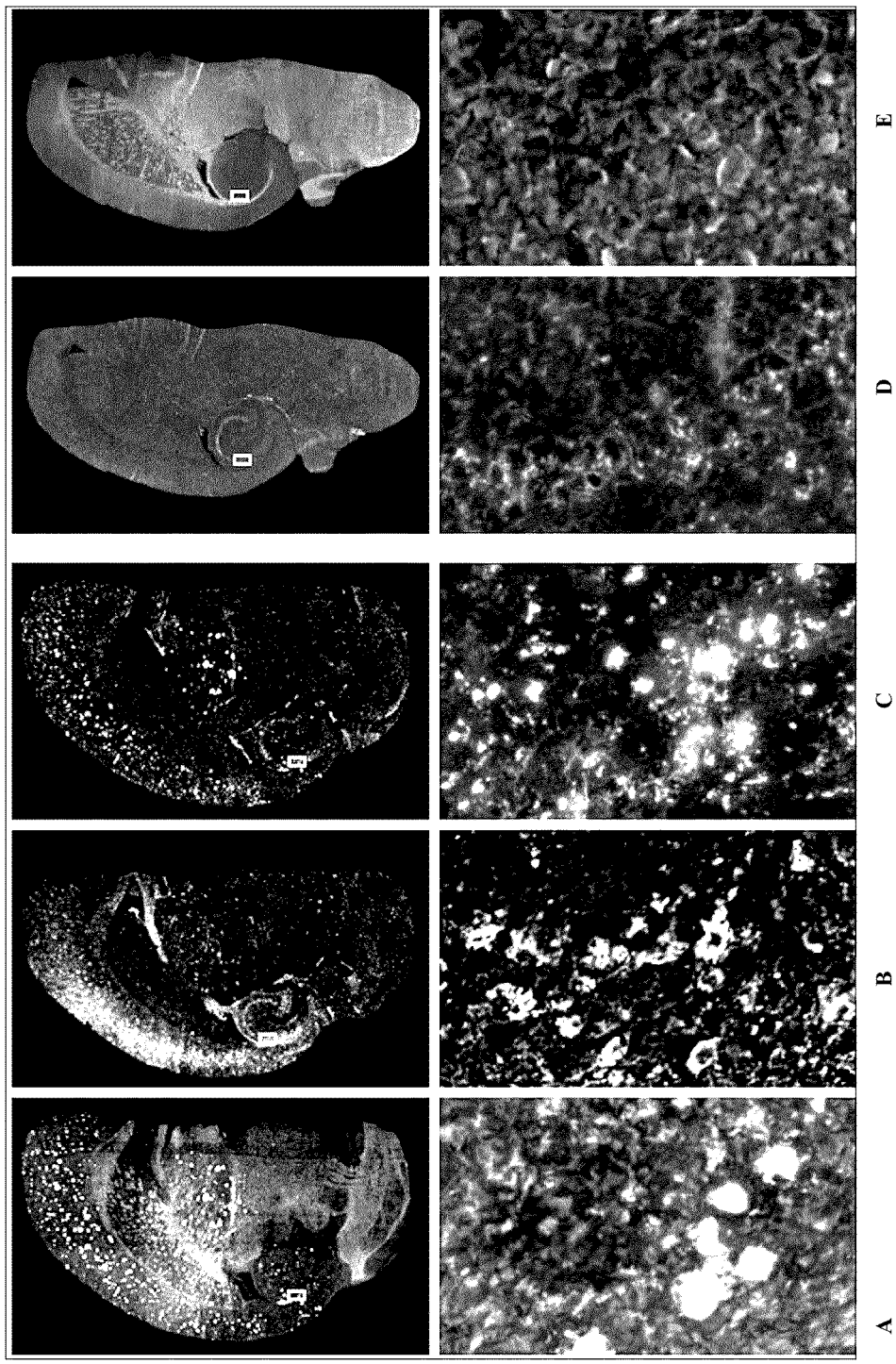
FIG. 4: Ex vivo APP/PS1-tau triple transgenic mouse model of AD (images A-C) and age matched control mouse (images D, E) brain (24 month old) 45 min p.i., 0.6 mg of compound 2 (in DMSO), cross-validated with thioflavin S (images A and E) stain of same slice and tau Antibody AT8 stain of a neighboring slice (images B) that confirms the compound targets Aβ and NFT in the mouse model. Magnification of hippocampus region proved the compound uptakes on Aβ and NFT in the mouse model.
Figure 5:
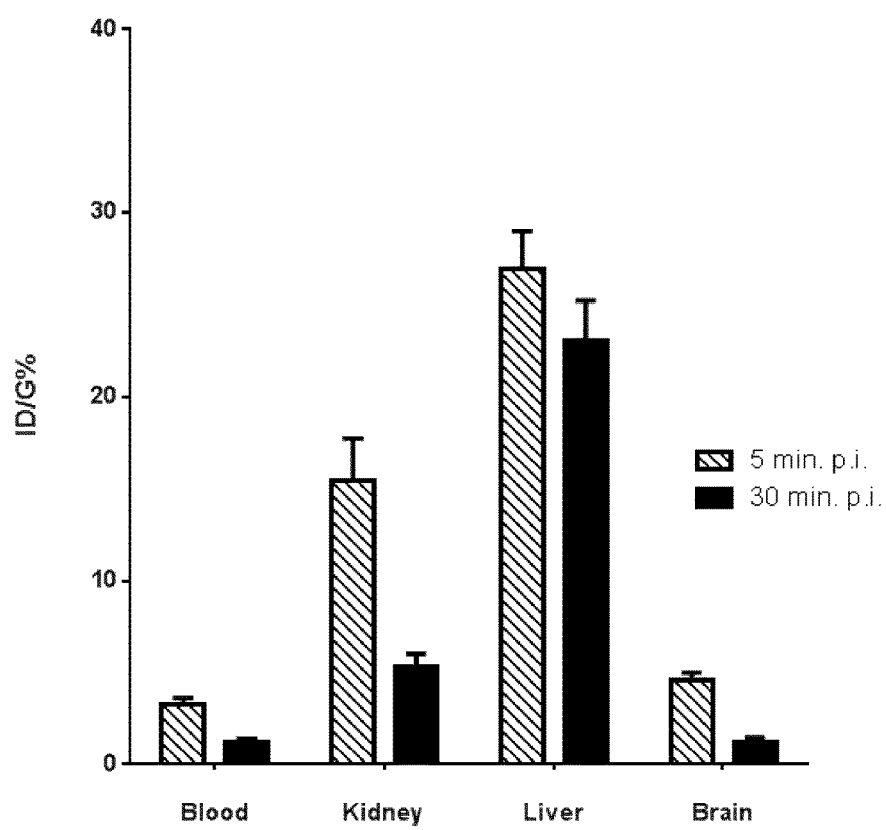
FIG. 5: Diagram showing the biodistribution of radiolabeled ([$^{11}$C]) compound 2, determined in wt bulb-c mice (n=5).

The invention claimed is:

1. A method of imaging a patient, the method comprising administering to the patient an amount of a compound of the following formula (I) or a pharmaceutically acceptable salt thereof

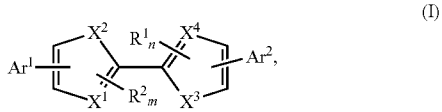

(I)

wherein:
$X^1$ and $X^4$ are independently selected from CH and N;
$X^2$ and $X^3$ are independently selected from $CH_2$, S and O;
$R^1$ and $R^2$ are independently selected from F, I, Br, and At, m and n are integers independently selected from 0 or 1;
$Ar^1$ and $Ar^2$ are independently aryl, heteroaryl, or a substituted version of either of these groups, wherein one or more hydrogen atom is replaced independently for each occurrence with a halogen, hydroxy, nitro, cyano, alkyl, haloalkyl, alkenyl, alkynyl, amino, alkylaryl, alkylamino, alkylamine, alkoxy, aryloxy;
—(O—$CH_2$—$CH_2$)$_o$—$R^{10}$, wherein $R^{10}$ is selected from —H, —OH, —$OSO_2$alkyl, —$OSO_2$aryl, and —F, and o is an integer from 1 to 4;
—$NR^{11}$COOalkyl,   —$NR^{11}$COOarylCOalkyl, —$NR^{11}$COaryl;
—COOalkyl, —COOaryl, —COalkyl, —COaryl, aryl, cycloalkyl;
cycloalkylamino-, -cycloalkylamine, heterocycle, a fluorescent label;
or —Z—$R^{12}$ substitutions wherein Z is selected from O, $NR^{13}$, NH and S;
and wherein $R^{11}$, $R^{12}$ and $R^{13}$ are independently selected from H, $C_nH_{2n+1}$, $C_nH_{2n}$-hal, with n being an integer of 1 to 3, —$CH_2$—CH=CH-hal, and —[$CH_2$—$CH_2$—O]$_p$—[$CH_2$—$CH_2$]$_q$-hal, wherein hal is selected from F, Cl, I, Br, and At, p is an integer of 1 to 3 and q is 1 or 2;
wherein suitable pairs of substituents attached to adjacent ring members of $Ar^1$ or $Ar^2$, respectively, can be combined to form a ring fused with $Ar^1$ or $Ar^2$;
wherein the compound of formula (I) or the pharmaceutically acceptable salt thereof is a radiolabeled compound, wherein one or more groups selected from $R^1$, $R^2$, a substituent attached to $Ar^1$ and a substituent attached to $Ar^2$ contain a radioisotope of an element which is present therein.

2. The method of claim 1, wherein $X^1$ and $X^4$ are both N, and $X^2$ and $X^3$ are independently selected from S and O.

3. The method of claim 1, wherein the compound corresponds to formula (II) or a pharmaceutically acceptable salt thereof:

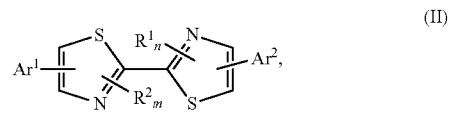

(II)

wherein $R^1$ and $R^2$ are independently selected from F, I, Br, and At, m and n are integers independently selected from 0 and 1;
$Ar^1$ and $Ar^2$ are independently aryl, heteroaryl, or a substituted version of either of these groups, wherein one or more hydrogen atom is replaced independently for each occurrence with a halogen, hydroxy, nitro, cyano, alkyl, haloalkyl, alkenyl, alkynyl, amino, alkylaryl, alkylamino, alkylamine, alkoxy, aryloxy;
—(O—$CH_2$—$CH_2$)$_o$—$R^{10}$, wherein $R^{10}$ is selected from —H, —OH, —$OSO_2$alkyl, —$OSO_2$aryl, and —F, and o is an integer from 1 to 4;
—$NR^{11}$COOalkyl,   —$NR^{11}$COOarylCOalkyl, —$NR^{11}$COaryl;
—COOalkyl, —COOaryl, —COalkyl, —COaryl, aryl, cycloalkyl;
cycloalkylamino-, -cycloalkylamine, heterocycle, a fluorescent label;
or —Z—$R^{12}$ substitutions wherein Z is selected from O, $NR^{13}$, NH and S;
and wherein $R^{11}$, $R^{12}$ and $R^{13}$ are independently selected from H, $C_nH_{2n+1}$, $C_nH_{2n}$-hal, with n being an integer of 1 to 3, —$CH_2$—CH=CH-hal, and —[$CH_2$—$CH_2$—O]$_p$—[$CH_2$—$CH_2$]$_q$-hal, wherein hal is selected from F, Cl, I, Br, and At, p is an integer of 1 to 3 and q is 1 or 2;
wherein suitable pairs of substituents attached to adjacent ring members of $Ar^1$ or $Ar^2$, respectively, can be combined to form a ring fused with $Ar^1$ or $Ar^2$;
wherein the compound of formula (II) or the pharmaceutically acceptable salt thereof is a radiolabeled compound, wherein one or more groups selected from $R^1$, $R^2$, a substituent attached to $Ar^1$ and a substituent attached to or $Ar^2$ contain a radioisotope of an element which is present therein.

4. The method of claim 1, wherein $R^1$ and $R^2$ are absent.

5. The method of claim 1, wherein the compound corresponds to formula (III) or a pharmaceutically acceptable salt thereof:

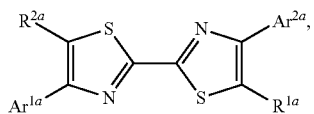

(III)

wherein
$R^{1a}$ and $R^{2a}$ are independently selected from H, F, I, Br, and At,
$Ar^{1a}$ and $Ar^{2a}$ are independently aryl, heteroaryl, or a substituted version of either of these groups, wherein one or more hydrogen atom is replaced independently for each occurrence with a halogen, hydroxy, alkyl, haloalkyl, alkenyl, alkynyl, alkylamino, alkylamine, alkoxy,
—(O—CH$_2$—CH$_2$)$_o$—R$^{10}$, wherein R$^{10}$ is selected from —H, —OH, —OSO$_2$alkyl, —OSO$_2$aryl, and —F, and o is an integer from 1 to 4;
or —Z—R$^{12}$ substitutions where Z is selected from O, NR$^{13}$, NH and S, and wherein R$^{12}$ and R$^{13}$ are independently selected from H, C$_n$H$_{2n+1}$, C$_n$H$_{2n}$-hal, with n being an integer of 1 to 3, —CH$_2$—CH=CH-hal, and —[CH$_2$—CH$_2$—O]$_p$—[CH$_2$—CH$_2$]$_q$-hal, wherein hal is selected from F, Cl, I, Br, and At, p is an integer of 1 to 3 and q is 1 or 2;
wherein suitable pairs of substituents attached to adjacent ring members of Ar$^{1a}$ or Ar$^{2a}$,
respectively, can be combined to form a ring fused with Ar$^{1a}$ or Ar$^{2a}$;
wherein the compound of formula (III) or the pharmaceutically acceptable salt thereof is a radiolabeled compound, wherein one or more groups selected from R$^{1a}$, R$^{2a}$, a substituent attached to Ar$^{1a}$ and a substituent attached to or Ar$^{2a}$ contain a radioisotope of an element which is present therein.

6. The method of claim 5, wherein R$^{1a}$ and R$^{2a}$ are H.

7. The method of claim 1, further comprising obtaining results indicating the presence or absence of a pathological condition in the patient associated with the formation of a neuropathological aggregate of peptides or proteins.

8. The method of claim 7, wherein the neuropathological aggregate of peptides or proteins is β-amyloid aggregates, neurofibrillary tangles of tau, or α-synuclein aggregates.

9. The method of claim 7, wherein the pathological condition is selected from Alzheimer's disease (AD) and Alzheimer's disease related dementia, Parkinson's disease (PD) and Parkinson's disease related dementia, frontotemporal dementias (FTDP), Creutzfeldt-Jakob disease (CJD) and Creutzfeldt-Jakob disease related dementia, Huntington's disease (HD) and Huntington's disease related dementia, and Lewy body disease (DLB) and Lewy body disease related dementia.

10. An in vitro method for the detection and/or quantification of neuropathological aggregates in a tissue sample obtained from a human or animal body, involving the steps of (i) contacting the tissue sample with compounds of formula (I) or a pharmaceutically acceptable salt thereof as defined in claim 1, and (ii) detecting and/or quantifying the compounds of formula (I) or a pharmaceutically acceptable salt thereof which have bound to the sample.

11. A diagnostic composition comprising a radiolabeled compound of formula (I) or a pharmaceutically acceptable salt thereof as defined in claim 1.

12. The diagnostic composition in accordance with claim 11, wherein X$^1$ and X$^4$ are both N, and X$^2$ and X$^3$ are independently selected from S and O.

13. The diagnostic composition of claim 11, wherein the compound is a compound of formula (II) or a pharmaceutically acceptable salt thereof:

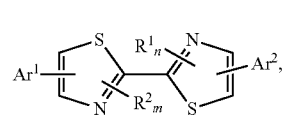

(II)

wherein R$^1$ and R$^2$ are independently selected from F, I, Br, and At, m and n are integers independently selected from 0 or 1;
Ar$^1$ and Ar$^2$ are independently aryl, heteroaryl, or a substituted version of either of these groups, wherein one or more hydrogen atom is replaced independently for each occurrence with a halogen, hydroxy, nitro, cyano, alkyl, haloalkyl, alkenyl, alkynyl, amino, alkylaryl, alkylamino, alkylamine, alkoxy, aryloxy;
—(O—CH$_2$—CH$_2$)$_o$—R$^{10}$, wherein R$^{10}$ is selected from —H, —OH, —OSO$_2$alkyl, —OSO$_2$aryl, and —F, and o is an integer from 1 to 4;
—NR$^{11}$COOalkyl, —NR$^{11}$COOarylCOalkyl, —NR$^{11}$COaryl;
—COOalkyl, —COOaryl, —COalkyl, —COaryl, aryl, cycloalkyl;
cycloalkylamino-, -cycloalkylamine, heterocycle, a fluorescent label;
or —Z—R$^{12}$ substitutions wherein Z is selected from O, NR$^{13}$, NH and S;
and wherein R$^{11}$, R$^{12}$ and R$^{13}$ are independently selected from H, C$_n$H$_{2n+1}$, C$_n$H$_{2n}$-hal, with n being an integer of 1 to 3, —CH$_2$—CH=CH-hal, and —[CH$_2$—CH$_2$—O]$_p$—[CH$_2$—CH$_2$]$_q$-hal, wherein hal is selected from F, Cl, I, Br, and At, p is an integer of 1 to 3 and q is 1 or 2;
wherein suitable pairs of substituents attached to adjacent ring members of Ar$^1$ or Ar$^2$,
respectively, can be combined to form a ring fused with Ar$^1$ or Ar$^2$;
and wherein one or more groups selected from R$^1$, R$^2$, a substituent attached to Ar$^1$ and a substituent attached to or Ar$^2$ contain a radioisotope of an element which is present therein.

14. The diagnostic composition of claim 11, wherein Ar$^1$ and Ar$^2$ are independently selected from phenyl, 5- or 6-membered heteroaryl, or substituted versions thereof.

15. The diagnostic composition of claim 11, wherein Ar$^1$ and Ar$^2$ each carry 1 or 2 substituents.

16. The diagnostic composition of claim 11, wherein R$^1$ and R$^2$ are absent.

17. The diagnostic composition in accordance with claim 11, wherein the compound is a compound of formula (III) or a pharmaceutically acceptable salt thereof:

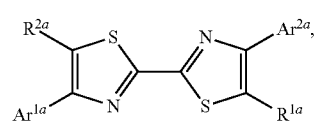

(III)

wherein
R$^{1a}$ and R$^{2a}$ are independently selected from H, F, I, Br, and At, $Ar^{1a}$ and $Ar^{2a}$ are independently aryl, heteroaryl, or a substituted version of either of these groups, wherein one or more hydrogen atom is replaced independently for each occurrence with a halogen, hydroxy, alkyl, haloalkyl, alkenyl, alkynyl, alkylamino, alkylamine, alkoxy, —(O—CH$_2$—CH$_2$)$_o$—R$^{10}$, wherein R$^{10}$ is selected from —H, —OH, —OSO$_2$alkyl, —OSO$_2$aryl, and —F, and o is an integer from 1 to 4;

or —Z—R$^{12}$ substitutions where Z is selected from O, NR$^{13}$, NH and S, and wherein R$^{12}$ and R$^{13}$ are independently selected from H, $C_nH_{2n+1}$, $C_nH_{2n}$-hal, with n being an integer of 1 to 3, —CH$_2$—CH=CH-hal, and —[CH$_2$—CH$_2$—O]$_p$—[CH$_2$—CH$_2$]-hal, wherein hal is selected from F, Cl, I, Br, and At, p is an integer of 1 to 3 and q is 1 or 2;

wherein suitable pairs of substituents attached to adjacent ring members of $Ar^{1a}$ or $Ar^{2a}$, respectively, can be combined to form a ring fused with $Ar^{1a}$ or $Ar^{2a}$;

and wherein one or more groups selected from $R^{1a}$, $R^{2a}$, a substituent attached to $Ar^{1a}$ and a substituent attached to or $Ar^{2a}$ contain a radioisotope of an element which is present therein.

18. The diagnostic composition in accordance with claim 15, wherein $R^{1a}$ and $R^{2a}$ are H.

19. The diagnostic composition of claim 11, wherein 20 mol % or more of the total amount of the compound of formula (I) or a pharmaceutically acceptable salt form thereof contain a radioisotope.

* * * * *